United States Patent
Horvath et al.

(10) Patent No.: US 10,667,947 B2
(45) Date of Patent: Jun. 2, 2020

(54) INTRAOCULAR DRUG DELIVERY

(71) Applicant: AqueSys, Inc., Aliso Viejo, CA (US)

(72) Inventors: Christopher Horvath, Mission Viejo, CA (US); Laszlo O. Romoda, San Clemente, CA (US)

(73) Assignee: AQUESYS, INC., Aliso Viejo, CA (US)

(*) Notice: Subject to any disclaimer, the term of this patent is extended or adjusted under 35 U.S.C. 154(b) by 409 days.

(21) Appl. No.: 15/613,018

(22) Filed: Jun. 2, 2017

(65) Prior Publication Data

US 2017/0348150 A1   Dec. 7, 2017

Related U.S. Application Data

(60) Provisional application No. 62/344,899, filed on Jun. 2, 2016.

(51) Int. Cl.
| | |
|---|---|
| *A61F 9/00* | (2006.01) |
| *A61F 9/007* | (2006.01) |
| *A61K 9/00* | (2006.01) |
| *A61L 27/22* | (2006.01) |
| *A61L 27/28* | (2006.01) |
| *A61L 27/54* | (2006.01) |

(52) U.S. Cl.
CPC ........ *A61F 9/00781* (2013.01); *A61F 9/0017* (2013.01); *A61K 9/0051* (2013.01); *A61L 27/222* (2013.01); *A61L 27/28* (2013.01); *A61L 27/54* (2013.01); *A61F 2250/0067* (2013.01); *A61F 2250/0068* (2013.01); *A61L 2430/16* (2013.01)

(58) Field of Classification Search
CPC .... A61F 9/00781; A61F 9/007; A61F 9/0017; A61K 9/0051; A61L 27/222; A61L 27/28; A61L 27/54
See application file for complete search history.

(56) References Cited

U.S. PATENT DOCUMENTS

| | | |
|---|---|---|
| 3,788,327 A | 1/1974 | Donowitz et al. |
| 3,960,150 A | 6/1976 | Hussain et al. |
| 4,090,530 A | 5/1978 | Lange |
| 4,402,308 A | 9/1983 | Scott |
| 4,562,463 A | 12/1985 | Lipton |

(Continued)

FOREIGN PATENT DOCUMENTS

| | | |
|---|---|---|
| CN | 1402625 | 3/2003 |
| CN | 101677823 | 3/2010 |

(Continued)

OTHER PUBLICATIONS

Written Opinion of the International Searching Authority (WO/ISA), dated Oct. 31, 2017, 10 pages.

(Continued)

*Primary Examiner* — Philip R Wiest
(74) *Attorney, Agent, or Firm* — Nathan S. Smith; Danny Mansour; Morgan, Lewis & Bockius LLP

(57) ABSTRACT

An ab externo method of placing an intraocular implant into an eye can include advancing a needle, in which the implant is disposed, into the eye through conjunctiva and sclera of the eye. The implant can include a drug deliverable to the eye. The implant can thereafter be released to be anchored in the eye and elute the drug to the eye.

22 Claims, 11 Drawing Sheets

(56) References Cited

U.S. PATENT DOCUMENTS

| | | |
|---|---|---|
| 4,583,117 A | 4/1986 | Lipton et al. |
| 4,700,692 A | 10/1987 | Baumgartner |
| 4,722,724 A | 2/1988 | Schocket |
| 4,744,362 A | 5/1988 | Grundler |
| 4,750,901 A | 6/1988 | Molteno |
| 4,787,885 A | 11/1988 | Binder |
| 4,804,382 A | 2/1989 | Turina et al. |
| 4,820,626 A | 4/1989 | Williams et al. |
| 4,826,478 A | 5/1989 | Schocket |
| 4,836,201 A | 6/1989 | Palton et al. |
| 4,848,340 A | 7/1989 | Bille et al. |
| 4,863,457 A | 9/1989 | Lee |
| 4,902,292 A | 2/1990 | Joseph |
| 4,911,161 A | 3/1990 | Schechter |
| 4,915,684 A | 4/1990 | MacKeen et al. |
| 4,934,363 A | 6/1990 | Smith et al. |
| 4,936,825 A | 6/1990 | Ungerleider |
| 4,946,436 A | 8/1990 | Smith |
| 4,968,296 A | 11/1990 | Ritch et al. |
| 4,978,352 A | 12/1990 | Fedorov et al. |
| 5,041,081 A | 8/1991 | Odrich |
| 5,057,098 A | 10/1991 | Zelman |
| 5,071,408 A | 12/1991 | Ahmed |
| 5,092,837 A | 3/1992 | Ritch et al. |
| 5,098,426 A | 3/1992 | Sklar et al. |
| 5,098,443 A | 3/1992 | Parel et al. |
| 5,162,641 A | 11/1992 | Fountain |
| 5,178,604 A | 1/1993 | Baerveldt et al. |
| 5,180,362 A | 1/1993 | Worst |
| 5,201,750 A | 4/1993 | Hocherl et al. |
| 5,207,660 A | 5/1993 | Lincoff |
| 5,273,530 A | 12/1993 | Del Cerro |
| 5,275,622 A | 1/1994 | Lazarus et al. |
| 5,290,295 A | 3/1994 | Querals et al. |
| 5,300,020 A | 4/1994 | L'Esperance, Jr. |
| 5,333,619 A | 8/1994 | Burgio |
| 5,338,291 A | 8/1994 | Speckman et al. |
| 5,342,370 A | 8/1994 | Simon et al. |
| 5,360,339 A | 11/1994 | Rosenberg |
| 5,368,015 A | 11/1994 | Wilk |
| 5,370,607 A | 12/1994 | Memmen |
| 5,399,951 A | 3/1995 | Lavallee et al. |
| 5,410,638 A | 4/1995 | Colgate et al. |
| 5,443,505 A | 8/1995 | Wong et al. |
| 5,472,439 A | 12/1995 | Hurd |
| 5,476,445 A | 12/1995 | Baerveldt et al. |
| 5,516,522 A | 5/1996 | Peyman et al. |
| 5,520,631 A | 5/1996 | Nordquist et al. |
| 5,558,629 A | 9/1996 | Baerveldt et al. |
| 5,558,630 A | 9/1996 | Fisher |
| 5,601,094 A | 2/1997 | Reiss |
| 5,656,026 A | 8/1997 | Joseph |
| 5,665,093 A | 9/1997 | Atkins et al. |
| 5,665,114 A | 9/1997 | Weadock et al. |
| 5,670,161 A | 9/1997 | Healy et al. |
| 5,688,562 A | 11/1997 | Hsiung |
| 5,695,474 A | 12/1997 | Daugherty |
| 5,704,907 A | 1/1998 | Nordquist et al. |
| 5,707,376 A | 1/1998 | Kavteladze et al. |
| 5,722,948 A | 3/1998 | Gross |
| 5,763,491 A | 6/1998 | Brandt et al. |
| 5,868,697 A | 2/1999 | Richter et al. |
| 5,908,449 A | 6/1999 | Bruchman et al. |
| 5,932,299 A | 8/1999 | Katoot |
| 5,938,583 A | 8/1999 | Grimm |
| 5,964,747 A | 10/1999 | Eaton et al. |
| 6,007,511 A | 12/1999 | Prywes |
| 6,007,578 A | 12/1999 | Schachar |
| 6,050,970 A | 4/2000 | Baerveldt |
| 6,086,543 A | 7/2000 | Anderson et al. |
| 6,102,045 A | 8/2000 | Nordquist et al. |
| 6,146,366 A | 11/2000 | Schachar |
| 6,159,218 A | 12/2000 | Aramant et al. |
| 6,165,210 A | 12/2000 | Lau et al. |
| 6,203,513 B1 | 3/2001 | Yaron et al. |
| 6,228,023 B1 | 5/2001 | Zaslavsky et al. |
| 6,228,873 B1 | 5/2001 | Brandt et al. |
| 6,261,256 B1 | 7/2001 | Ahmed |
| 6,264,665 B1 | 7/2001 | Yu et al. |
| 6,280,468 B1 | 8/2001 | Schachar |
| 6,413,540 B1 | 7/2002 | Yaacobi |
| 6,450,937 B1 | 9/2002 | Mercereau et al. |
| 6,471,666 B1 | 10/2002 | Odrich |
| 6,483,930 B1 | 11/2002 | Musgrave et al. |
| 6,514,238 B1 | 2/2003 | Hughes |
| 6,524,275 B1 | 2/2003 | Lynch et al. |
| 6,533,768 B1 | 3/2003 | Hill |
| 6,544,249 B1 | 4/2003 | Yu et al. |
| 6,558,342 B1 | 5/2003 | Yaron et al. |
| 6,595,945 B2 | 7/2003 | Brown |
| 6,638,239 B1 | 10/2003 | Bergheim et al. |
| 6,699,210 B2 | 3/2004 | Williams et al. |
| 6,726,664 B2 | 4/2004 | Yaron et al. |
| D490,152 S | 5/2004 | Myall et al. |
| 6,736,791 B1 | 5/2004 | Tu et al. |
| 6,752,753 B1 | 6/2004 | Hoskins et al. |
| 6,881,198 B2 | 4/2005 | Brown |
| 6,936,053 B1 | 8/2005 | Weiss |
| 6,939,298 B2 | 9/2005 | Brown et al. |
| 7,008,396 B1 | 3/2006 | Straub |
| 7,037,335 B2 | 5/2006 | Freeman et al. |
| 7,041,077 B2 | 5/2006 | Shields |
| 7,094,225 B2 | 8/2006 | Tu et al. |
| 7,118,547 B2 | 10/2006 | Dahan |
| 7,135,009 B2 | 11/2006 | Tu et al. |
| 7,163,543 B2 | 1/2007 | Smedley et al. |
| 7,186,232 B1 | 3/2007 | Smedley et al. |
| 7,207,980 B2 | 4/2007 | Christian et al. |
| 7,291,125 B2 | 11/2007 | Coroneo |
| 7,331,984 B2 | 2/2008 | Tu et al. |
| 7,431,709 B2 | 10/2008 | Pinchuk et al. |
| 7,431,710 B2 | 10/2008 | Tu et al. |
| 7,458,953 B2 | 12/2008 | Peyman |
| 7,488,303 B1 | 2/2009 | Haffner et al. |
| 7,594,899 B2 | 9/2009 | Pinchuk et al. |
| 7,625,384 B2 | 12/2009 | Eriksson et al. |
| 7,658,729 B2 | 2/2010 | Hull |
| 7,708,711 B2 | 5/2010 | Tu et al. |
| 7,722,549 B2 | 5/2010 | Nakao |
| 7,837,644 B2 | 11/2010 | Pinchuk et al. |
| 7,867,186 B2 | 1/2011 | Haffner et al. |
| 7,892,282 B2 | 2/2011 | Shepherd |
| 8,109,896 B2 | 2/2012 | Nissan et al. |
| 8,267,882 B2 | 9/2012 | Euteneuer et al. |
| 8,277,437 B2 | 10/2012 | Saal et al. |
| 8,308,701 B2 | 11/2012 | Horvath et al. |
| 8,313,454 B2 | 11/2012 | Yaron et al. |
| 8,337,393 B2 | 12/2012 | Silverstrini et al. |
| 8,337,509 B2 | 12/2012 | Schieber et al. |
| 8,377,122 B2 | 2/2013 | Silvestrini et al. |
| 8,425,449 B2 | 4/2013 | Wardle et al. |
| 8,444,589 B2 | 5/2013 | Silvestrini |
| 8,486,000 B2 | 7/2013 | Coroneo |
| 8,506,515 B2 | 8/2013 | Burns et al. |
| 8,512,404 B2 | 8/2013 | Frion et al. |
| 8,529,492 B2 | 9/2013 | Clauson et al. |
| 8,535,333 B2 | 9/2013 | de Juan, Jr. et al. |
| 8,545,430 B2 | 10/2013 | Silvestrini |
| 8,585,629 B2 | 11/2013 | Grabner et al. |
| 8,663,303 B2 | 3/2014 | Horvath et al. |
| 8,721,702 B2 | 5/2014 | Romoda et al. |
| 8,758,290 B2 | 6/2014 | Horvath et al. |
| 8,765,210 B2 | 7/2014 | Romoda et al. |
| 8,801,766 B2 | 8/2014 | Reitsamer et al. |
| 8,828,070 B2 | 9/2014 | Romoda et al. |
| 8,852,136 B2 | 10/2014 | Horvath et al. |
| 8,852,137 B2 | 10/2014 | Horvath et al. |
| 8,852,256 B2 | 10/2014 | Horvath et al. |
| 8,974,511 B2 | 3/2015 | Horvath et al. |
| 9,017,276 B2 | 4/2015 | Horvath et al. |
| 9,044,301 B1 | 6/2015 | Pinchuk et al. |
| 9,095,411 B2 | 8/2015 | Horvath et al. |
| 9,095,413 B2 | 8/2015 | Romoda et al. |
| 9,192,516 B2 | 11/2015 | Horvath et al. |

(56) References Cited

U.S. PATENT DOCUMENTS

| | | |
|---|---|---|
| 9,271,869 B2 | 3/2016 | Horvath et al. |
| 9,283,116 B2 | 3/2016 | Romoda et al. |
| 9,326,891 B2 | 5/2016 | Horvath et al. |
| 9,393,153 B2 | 7/2016 | Horvath et al. |
| 2001/0025150 A1 | 9/2001 | de Juan et al. |
| 2001/0056254 A1 | 12/2001 | Cragg et al. |
| 2002/0087149 A1 | 7/2002 | McCary |
| 2002/0099434 A1 | 7/2002 | Buscemi et al. |
| 2002/0133168 A1 | 9/2002 | Smedley et al. |
| 2003/0015203 A1 | 1/2003 | Makower et al. |
| 2003/0050574 A1 | 3/2003 | Krueger |
| 2003/0060752 A1 | 3/2003 | Bergheim et al. |
| 2003/0093084 A1 | 5/2003 | Nissan et al. |
| 2003/0097053 A1 | 5/2003 | Itoh |
| 2003/0187383 A1 | 10/2003 | Weber et al. |
| 2003/0236483 A1 | 12/2003 | Ren |
| 2003/0236484 A1 | 12/2003 | Lynch et al. |
| 2004/0077987 A1 | 4/2004 | Rapacki et al. |
| 2004/0147870 A1 | 7/2004 | Burns et al. |
| 2004/0199130 A1 | 10/2004 | Chornenky et al. |
| 2004/0210209 A1 | 10/2004 | Yeung et al. |
| 2004/0215133 A1 | 10/2004 | Weber et al. |
| 2004/0216749 A1 | 11/2004 | Tu |
| 2004/0236343 A1 | 11/2004 | Taylor et al. |
| 2004/0254521 A1 | 12/2004 | Simon |
| 2004/0260227 A1 | 12/2004 | Lisk et al. |
| 2005/0049578 A1 | 3/2005 | Tu et al. |
| 2005/0101967 A1 | 5/2005 | Weber et al. |
| 2005/0143363 A1 | 6/2005 | De Juan et al. |
| 2005/0246023 A1 | 11/2005 | Yeung |
| 2005/0267398 A1 | 12/2005 | Protopsaltis et al. |
| 2005/0271704 A1 | 12/2005 | Tu et al. |
| 2005/0277864 A1 | 12/2005 | Haffner et al. |
| 2006/0052721 A1 | 3/2006 | Dunker et al. |
| 2006/0064112 A1 | 3/2006 | Perez |
| 2006/0106370 A1 | 5/2006 | Baerveldt et al. |
| 2006/0116625 A1 | 6/2006 | Renati et al. |
| 2006/0149194 A1 | 7/2006 | Conston et al. |
| 2006/0155238 A1 | 7/2006 | Shields |
| 2006/0173397 A1 | 8/2006 | Tu et al. |
| 2006/0173446 A1 | 8/2006 | Dacquay et al. |
| 2006/0200113 A1 | 9/2006 | Haffner et al. |
| 2006/0241411 A1 | 10/2006 | Field et al. |
| 2007/0027537 A1 | 2/2007 | Castillejos |
| 2007/0093783 A1 | 4/2007 | Kugler et al. |
| 2007/0118065 A1 | 5/2007 | Pinchuk et al. |
| 2007/0141116 A1 | 6/2007 | Pinchuk et al. |
| 2007/0172903 A1 | 7/2007 | Toner et al. |
| 2007/0191863 A1 | 8/2007 | De Juan et al. |
| 2007/0202186 A1 | 8/2007 | Yamamoto et al. |
| 2007/0263172 A1 | 11/2007 | Mura |
| 2007/0293872 A1 | 12/2007 | Peyman |
| 2008/0015633 A1 | 1/2008 | Abbott et al. |
| 2008/0027304 A1 | 1/2008 | Pardo et al. |
| 2008/0057106 A1 | 3/2008 | Erickson et al. |
| 2008/0108933 A1 | 5/2008 | Yu et al. |
| 2008/0147001 A1 | 6/2008 | Al-Marashi et al. |
| 2008/0181929 A1 | 7/2008 | Robinson et al. |
| 2008/0249467 A1 | 10/2008 | Burnett et al. |
| 2008/0281277 A1 | 11/2008 | Thyzel |
| 2008/0312661 A1 | 12/2008 | Downer et al. |
| 2009/0036818 A1 | 2/2009 | Grahn et al. |
| 2009/0043321 A1 | 2/2009 | Conston et al. |
| 2009/0124973 A1 | 5/2009 | D'Agostino et al. |
| 2009/0182421 A1 | 7/2009 | Silvestrini et al. |
| 2009/0209910 A1 | 8/2009 | Kugler et al. |
| 2009/0216106 A1 | 8/2009 | Takii |
| 2009/0264813 A1 | 10/2009 | Chang |
| 2009/0270890 A1 | 10/2009 | Robinson et al. |
| 2009/0281520 A1 | 11/2009 | Highley et al. |
| 2009/0287136 A1 | 11/2009 | Castillejos |
| 2010/0004581 A1 | 1/2010 | Brigatti et al. |
| 2010/0063478 A1 | 3/2010 | Selkee |
| 2010/0098772 A1 | 4/2010 | Robinson et al. |
| 2010/0100104 A1 | 4/2010 | Yu et al. |
| 2010/0119696 A1 | 5/2010 | Yu et al. |
| 2010/0121248 A1 | 5/2010 | Yu et al. |
| 2010/0121249 A1 | 5/2010 | Yu et al. |
| 2010/0134759 A1 | 6/2010 | Silvestrini et al. |
| 2010/0137981 A1 | 6/2010 | Silvestrini et al. |
| 2010/0173866 A1 | 7/2010 | Hee et al. |
| 2010/0191103 A1 | 7/2010 | Stamper et al. |
| 2010/0191224 A1 | 7/2010 | Butcher |
| 2010/0249691 A1 | 9/2010 | Van Der Mooren et al. |
| 2010/0274259 A1* | 10/2010 | Yaron .................. A61F 9/00781 606/108 |
| 2010/0328606 A1 | 12/2010 | Peyman |
| 2011/0009874 A1 | 1/2011 | Wardle et al. |
| 2011/0046536 A1 | 2/2011 | Stegmann et al. |
| 2011/0098627 A1 | 4/2011 | Wilcox |
| 2011/0105990 A1 | 5/2011 | Silvestrini |
| 2011/0118745 A1 | 5/2011 | Yu et al. |
| 2011/0118835 A1 | 5/2011 | Silvestrini et al. |
| 2011/0230890 A1 | 9/2011 | Thyzel |
| 2011/0234976 A1 | 9/2011 | Kocaoglu et al. |
| 2012/0078362 A1 | 3/2012 | Haffner et al. |
| 2012/0123315 A1 | 5/2012 | Horvath et al. |
| 2012/0123316 A1 | 5/2012 | Horvath et al. |
| 2012/0123317 A1 | 5/2012 | Horvath et al. |
| 2012/0123434 A1 | 5/2012 | Grabner et al. |
| 2012/0165720 A1 | 6/2012 | Horvath et al. |
| 2012/0165933 A1 | 6/2012 | Haffner et al. |
| 2012/0197175 A1 | 8/2012 | Horvath et al. |
| 2012/0226150 A1 | 9/2012 | Balicki et al. |
| 2012/0310137 A1 | 12/2012 | Silvestrini |
| 2013/0158462 A1 | 6/2013 | Wardle et al. |
| 2013/0184631 A1 | 7/2013 | Pinchuk |
| 2013/0245573 A1 | 9/2013 | de Juan, Jr. et al. |
| 2013/0253528 A1 | 9/2013 | Haffner et al. |
| 2013/0281817 A1 | 10/2013 | Schaller et al. |
| 2013/0281908 A1 | 10/2013 | Schaller et al. |
| 2014/0066833 A1 | 3/2014 | Yaron et al. |
| 2014/0081195 A1 | 3/2014 | Clauson et al. |
| 2014/0135916 A1 | 5/2014 | Clauson et al. |
| 2014/0213958 A1 | 7/2014 | Clauson et al. |
| 2014/0236066 A1 | 8/2014 | Horvath et al. |
| 2014/0236067 A1* | 8/2014 | Horvath .................. A61F 9/007 604/9 |
| 2014/0243730 A1* | 8/2014 | Horvath .............. A61F 9/00781 604/8 |
| 2014/0275923 A1 | 9/2014 | Haffner et al. |
| 2014/0276332 A1 | 9/2014 | Crimaldi et al. |
| 2014/0277349 A1 | 9/2014 | Vad |
| 2014/0303544 A1 | 10/2014 | Haffner et al. |
| 2014/0323995 A1 | 10/2014 | Clauson et al. |
| 2014/0343476 A1 | 11/2014 | Penhasi |
| 2014/0371651 A1 | 12/2014 | Pinchuk |
| 2015/0005689 A1 | 1/2015 | Horvath et al. |
| 2015/0011926 A1 | 1/2015 | Reitsamer et al. |
| 2015/0038893 A1 | 2/2015 | Haffner et al. |
| 2015/0133946 A1 | 5/2015 | Horvath et al. |
| 2015/0238687 A1 | 8/2015 | Novakovic et al. |
| 2015/0290035 A1 | 10/2015 | Horvath et al. |
| 2015/0374545 A1 | 12/2015 | Horvath et al. |
| 2016/0135993 A1 | 5/2016 | Horvath et al. |
| 2016/0135994 A1 | 5/2016 | Romoda et al. |
| 2016/0158063 A1 | 6/2016 | Romoda et al. |
| 2016/0250071 A1 | 9/2016 | Horvath et al. |
| 2016/0256317 A1 | 9/2016 | Horvath et al. |
| 2016/0256318 A1 | 9/2016 | Horvath et al. |
| 2016/0256319 A1 | 9/2016 | Horvath et al. |
| 2016/0256320 A1 | 9/2016 | Horvath et al. |
| 2016/0256323 A1 | 9/2016 | Horvath et al. |
| 2016/0278982 A1 | 9/2016 | Horvath et al. |
| 2016/0354244 A1 | 12/2016 | Horvath et al. |
| 2016/0354245 A1 | 12/2016 | Horvath et al. |
| 2017/0172797 A1 | 6/2017 | Horvath et al. |
| 2017/0172798 A1 | 6/2017 | Horvath et al. |

(56) References Cited

U.S. PATENT DOCUMENTS

| | | |
|---|---|---|
| 2017/0172799 A1 | 6/2017 | Horvath |
| 2017/0348150 A1 | 12/2017 | Horvath et al. |

FOREIGN PATENT DOCUMENTS

| | | |
|---|---|---|
| CN | 102481171 | 5/2012 |
| CN | 102510746 | 6/2012 |
| GB | 2 296 663 A | 7/1996 |
| JP | 2009-523540 | 6/2009 |
| JP | 2012-527318 | 11/2012 |
| RU | 2313315 C2 | 12/2007 |
| RU | 2482822 | 5/2013 |
| WO | WO-98/23237 A1 | 6/1998 |
| WO | WO-2000/056255 | 9/2000 |
| WO | WO-2002/74052 A2 | 9/2002 |
| WO | WO-2007/087061 A2 | 8/2007 |
| WO | WO-2008/005873 A2 | 1/2008 |
| WO | WO 2010/003011 | 1/2010 |
| WO | WO 2011/155922 | 12/2011 |
| WO | WO 2016/023942 | 2/2016 |
| WO | WO 2016/159999 | 10/2016 |
| WO | WO2016196841 | 12/2016 |

OTHER PUBLICATIONS

Coran, Pediatric Surgery, vol. e, 7 th edition, published on Feb. 14, 2012, pp. 1673-1697.

Quere, "Fluid Coating on a Fiber," Annu. Rev. Fluid Mech. 1999, 31:347-84.

Horvath, U.S. Appl. No. 15/703,802, "Intraocular Shunt Implantation," filed Sep. 13, 2017.

Horvath, U.S. Appl. No. 15/807,503, "Manually Adjustable Intraocular Flow Regulation," filed Nov. 8, 2017.

* cited by examiner

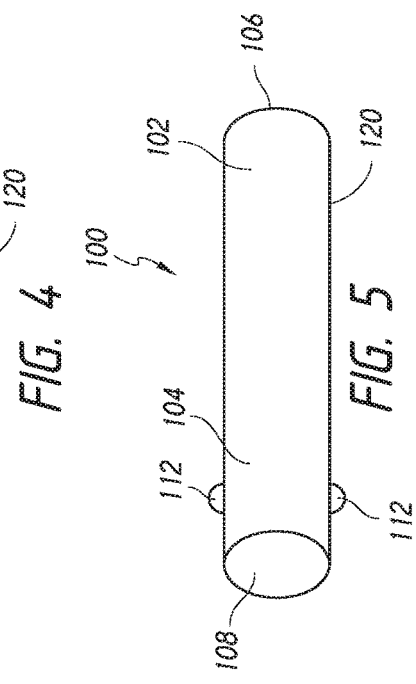
FIG. 2
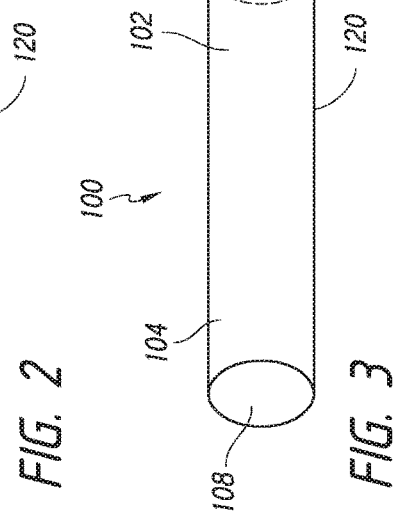
FIG. 3
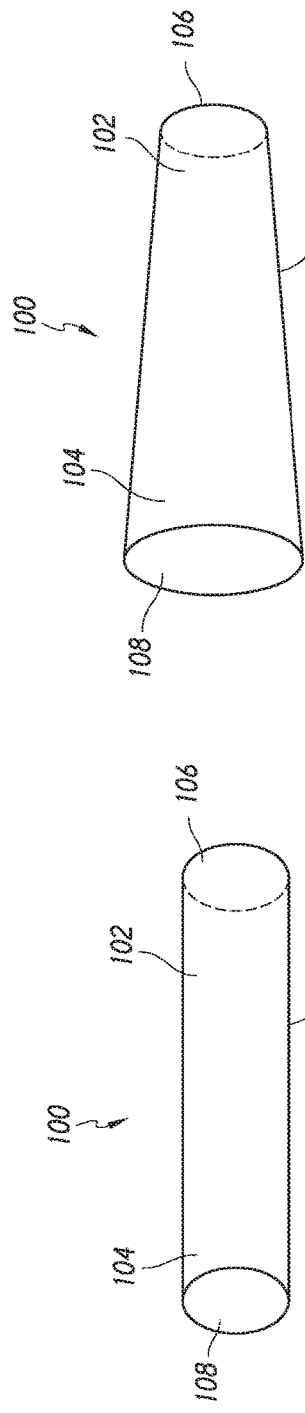
FIG. 4
FIG. 5
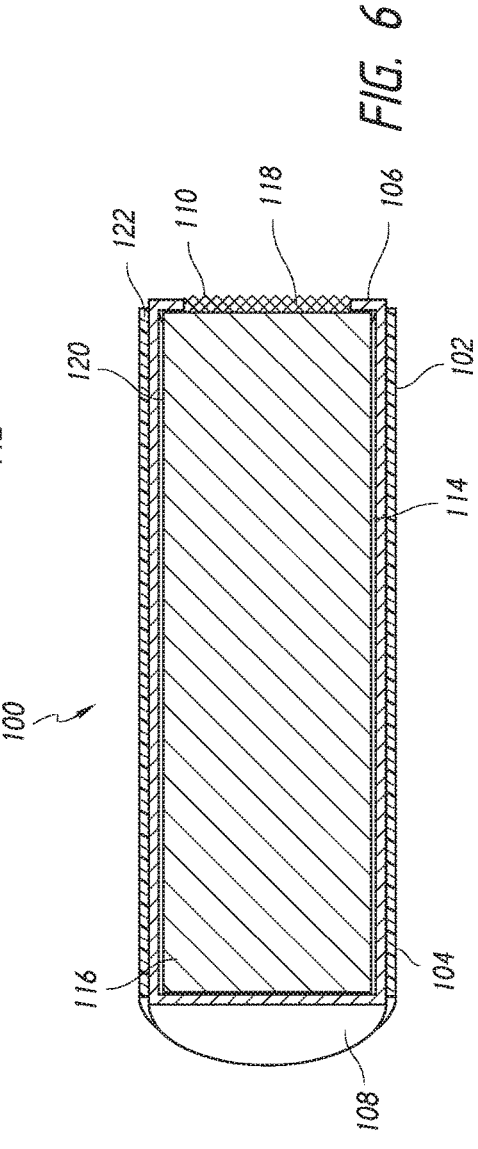
FIG. 6

INTRAOCULAR DRUG DELIVERY

CROSS-REFERENCE TO RELATED APPLICATIONS

This application claims the benefit of and priority to related U.S. Patent Provisional Application No. 62/344,899, filed on Jun. 2, 2016, the entirety of which is incorporated herein by reference.

BACKGROUND

Field

The present disclosure generally relates to delivering an intraocular implant into an eye, and more specifically, to methods and devices for ab externo implantation of a drug-eluting intraocular implant or a shunt without the creation of a scleral slit or conjunctival dissection.

Description of the Related Art

Glaucoma is a disease of the eye that affects millions of people. Glaucoma is associated with an increase in intraocular pressure resulting either from a failure of a drainage system of an eye to adequately remove aqueous humor from an anterior chamber of the eye or overproduction of aqueous humor by a ciliary body in the eye. Build-up of aqueous humor and resulting intraocular pressure may result in irreversible damage to the optic nerve and the retina, which may lead to irreversible retinal damage and blindness.

Glaucoma may be treated in a number of different ways. One manner of treatment involves delivery of drugs such as beta-blockers or prostaglandins to the eye to either reduce production of aqueous humor or increase flow of aqueous humor from an anterior chamber of the eye. Another treatment typically used to treat glaucoma involves a glaucoma filtration surgery. The procedure involves placing a shunt in the eye to relieve intraocular pressure by creating a pathway for draining aqueous humor from the anterior chamber of the eye. The shunt is typically positioned in the eye such that it creates a drainage pathway between the anterior chamber of the eye and a region of lower pressure. Such fluid flow pathways allow for aqueous humor to exit the anterior chamber.

The importance of lowering intraocular pressure (IOP) in delaying glaucomatous progression has been well documented. When conventional drug therapy fails, or is not tolerated, surgical intervention is warranted. There are various surgical filtration methods for lowering intraocular pressure by creating a fluid flow-path between the anterior chamber and the subconjunctival tissue. In one particular method, an intraocular shunt is positioned in the eye to drain fluid from the anterior chamber to locations such as the sub-Tenon's space, the subconjunctival space, the episcleral vein, the suprachoroidal space, Schlemm's canal, and the intrascleral space.

Methods of implanting intraocular implants are known in the art. Implants may be implanted using an ab externo approach (entering through the conjunctiva and inwards through the sclera) or an ab interno approach (entering through the cornea, across the anterior chamber, through the trabecular meshwork and sclera). Further, various manual and automated deployment devices for implanting an intraocular implant have been described. Most deployment devices are coupled to a hollow needle which holds the intraocular implant. Whether an ab externo approach or an ab interno approach is used, the needle is inserted into the eye to deploy the intraocular implant into the eye. See, for example, U.S. Pat. No. 6,544,249, U.S. Patent Application Publication No. 2008/0108933, and U.S. Pat. No. 6,007,511, the entireties of which are incorporated herein by reference.

SUMMARY

Traditional ab externo approaches are shown for example in U.S. Pat. No. 8,109,896 to Nissan et al., U.S. Pat. No. 8,075,511 to Tu et al., and U.S. Pat. No. 7,879,001 to Haffner et al., the content of each of which is incorporated by reference herein in its entirety.

In such traditional surgeries, a distal end of a deployment device or injector is used to make a scleral flap or slit to access the eye. The conjunctiva can be dissected or pulled away from the sclera to expose the sclera. In some instances, this can allow the surgeon to cut and separate a small flap of the sclera away from the underlying sclera. A needle can then be inserted into the eye below the scleral flap to access the anterior angle of the eye. The needle is then withdrawn, leaving a scleral slit behind.

Thereafter, a silicone tube with sufficient stiffness is manually pushed through the scleral slit from the outside so that the distal tube ends distal to the trabecular meshwork in the anterior chamber of the eye. In some instances, the scleral flap can be repositioned over the proximal end of the tube and sutures can be used to re-secure the flap and conjunctiva. In other instances where only the conjunctiva is dissected, the proximal end of the tube can be positioned to exit the sclera, lay on top of it, and be connected to a plate that is fixated by sutures to the outside scleral surface (and within a pocket underlying the conjunctiva) far away (>10 mm) from the limbus.

Some of the problems associated with this surgery include the necessity to cauterize to avoid significant bleeding and the large size of the remaining silicone tube and plate. Due to the obtrusive nature of the silicone tube and plate, these can eventually cause the conjunctiva to erode, requiring a scleral graft to be placed over the silicone tube and plate.

The present disclosure provides various new methods and device concepts for an ab externo implantation of a drug-eluting intraocular implant or a drug-eluting intraocular shunt without the creation of a scleral slit or conjunctival dissection. It is contemplated that although particular embodiments may be disclosed or shown in the context of an intraocular shunt, the various approaches described herein can be modified to provide an implant that does not permit flow through the implant (e.g., a plug), or an implant that provides a flow path (e.g., a shunt).

In accordance with some embodiments, the present disclosure provides ab externo methods that can be used to safely position and anchor a drug-eluting implant into the eye. However, although some embodiments are presented as ab externo, some embodiments disclosed herein can also be performed via ab interno needle placement. In such embodiments, the positioning of the implant or shunt can be revised from an ab externo method (e.g., reversing the position of the ends of the implant if the implant is tapered or comprises anti-migration engagement features). Accordingly, the methods disclosed herein can be implemented either ab interno or ab externo and result in placement or anchoring of an implant within the sclera.

Accordingly, to some embodiments, the methods can therefore be performed to provide treatment with a drug or pharmaceutical, such as by implanting an intraocular implant that has been coated, packed, layered, and/or impregnated with a pharmaceutical and/or biological agent, by treating the eye topically with a pharmaceutical and/or biological agent, and/or by injecting a pharmaceutical and/or biological agent into the anterior chamber and/or a target outflow region, including any target outflow regions discussed or referenced herein, prior to or after releasing a implant from the device.

Suitable agents that can be used in some embodiments disclosed herein may include, for example, any of those disclosed in the following U.S. Pat. Nos. 8,785,394; 8,062,657; 7,799,336; 7,790,183; 7,033,605; 6,719,991; 6,558,686; 6,162,487; 5,902,283; 5,853,745; and 5,624,704; and U.S. Patent Publication No. 2008/0108933; the content of each of these references is incorporated by reference herein its entirety. Examples of suitable agents include antimitotic pharmaceuticals such as Mitomycin-C or 5-Fluorouracil, anti-VEGF (such as Lucintes, Macugen, Avastin, VEGF, or steroids), anticoagulants, antimetabolites, antimicrobial agents, angiogenesis inhibitors, steroids, anti-inflammatories, antibiotics, antiseptics, disinfectants, brimonidine, timolol, prostaglandin analogs (such as travoprost, latanoprost, and tafluprost), prostamides (such as bimatoprost), cyclosporin, pilocarpine, corticosteroids and other steroid derivatives (such as hydrocortisone, dexamethasone, beclomethasone dipropionate, triamcinolone, triamcinolone acetate, cortisol benzoate), or other agents or combinations thereof, for treating conditions of the eye, such as glaucoma, dry eye, allergy, or conjunctivitis, to name a few.

One of the aims is to create a simple and safe procedure that can be performed in an office setting. The methods provided by some embodiments can use an implant injector or deployment device similar in operation to the XEN Injector produced by Applicant. Further, the methods can be implemented using the injector by itself or by using the injector in combination with one or more injector placement devices, such as those disclosed in U.S. Patent Application Nos. 61/170,338, filed on Jun. 3, 2015, 62/279,585, filed on Jan. 15, 2016, U.S. Patent Application Publication No. 2016/0354244, filed on Jun. 2, 2016, and U.S. Patent Application Publication No. 2016/0354245, filed on Jun. 2, 2016, titled Ab Externo Intraocular Shunt Placement, the entirety of each of which is incorporated herein by reference.

According to some embodiments, ab externo procedures are provided herein that enable a portion of an intraocular implant or an outflow end of a shunt to be deployed under/into any of a variety of outflow regions without making a scleral flap or otherwise requiring a conjunctival dissection. Thus, the outflow end of the shunt can be positioned in target outflow regions including the subconjunctival space or over-Tenon's space (between Tenon's and conjunctiva), the suprascleral or sub-Tenon's space (between Tenon's and sclera), the intra-Tenon's space (between layers of Tenon's capsule, or in the intra-Tenon's adhesion space), the choroidal and suprachoroidal space, the intrascleral space (between layers of sclera), Schlemm's canal, the vitreous space, the episcleral vein, or the supraciliary space. Further, in accordance with some embodiments in which the outflow end of the shunt is placed in the intra-Tenon's adhesion space, the Tenon adhesions remain intact, just as they would for an ab interno approach. Thus, a needle of a shunt injector can pierce conjunctiva, sclera, and in some embodiments, Tenon's capsule, as it is advanced into the eye to position the shunt within the eye without creating a scleral flap or conjunctival dissection. For example, the shunt can provide fluid communication between the anterior chamber and a desired target outflow region.

Advantageously, some embodiments therefore provide methods and devices that place an intraocular shunt ab externo into the eye without requiring a low gauge silicone tube or diffusion plate attached to the tube, as used in the prior art. Instead, according to some embodiments, a higher gauge needle and intraocular shunt can be placed without causing significant trauma to the eye. The shunt can be inserted through the target outflow region and ejected from the needle such that an inflow end of the shunt resides in the anterior chamber of the eye and an outflow end of the needle resides in the target outflow region.

Moreover, as noted above, some embodiments can be performed using an intraocular implant placement device to facilitate positioning and maintaining an orientation of the implant relative to one or more aspects of the eye, as disclosed in U.S. Patent Application Nos. 61/170,338, filed on Jun. 3, 2015, 62/279,585, filed on Jan. 15, 2016, U.S. Patent Application Publication No. 2016/0354244, filed on Jun. 2, 2016, and U.S. Patent Application Publication No. 2016/0354245, filed on Jun. 2, 2016, titled Ab Externo Intraocular Shunt Placement, the entirety of each of which is incorporated herein by reference. The intraocular implant placement device can optionally comprise one or more structures that can facilitate positioning of the intraocular implant placement device onto or around the eye. Optionally, the intraocular implant placement device can comprise one or more features that can secure the implant placement device relative to the eye once a desired position has been achieved. In some embodiments, such features can be selectively activated once the implant placement device is in a desired position. Such features can include vacuum suction and/or surface friction elements (such as ridges, microhooks, or other such elements that can increase the surface contact and/or friction between the implant placement device and the eye). In some embodiments, suction and mechanical engagement can be used alone or together to enable the implant placement device to be coupled to or removably affixed to the eye.

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof as well as the appended drawings.

It is to be understood that both the foregoing general description and the following detailed description are exemplary and explanatory and are intended to provide further explanation of the subject technology.

BRIEF DESCRIPTION OF THE DRAWINGS

Various features of illustrative embodiments of the inventions are described below with reference to the drawings. The illustrated embodiments are intended to illustrate, but not to limit, the inventions. The drawings contain the following figures:

FIGS. 2-5 illustrate intraocular implants, according to some embodiments.

FIG. 6 illustrates a cross-sectional view of an intraocular implant, according to some embodiments.

DETAILED DESCRIPTION

Figure 1:
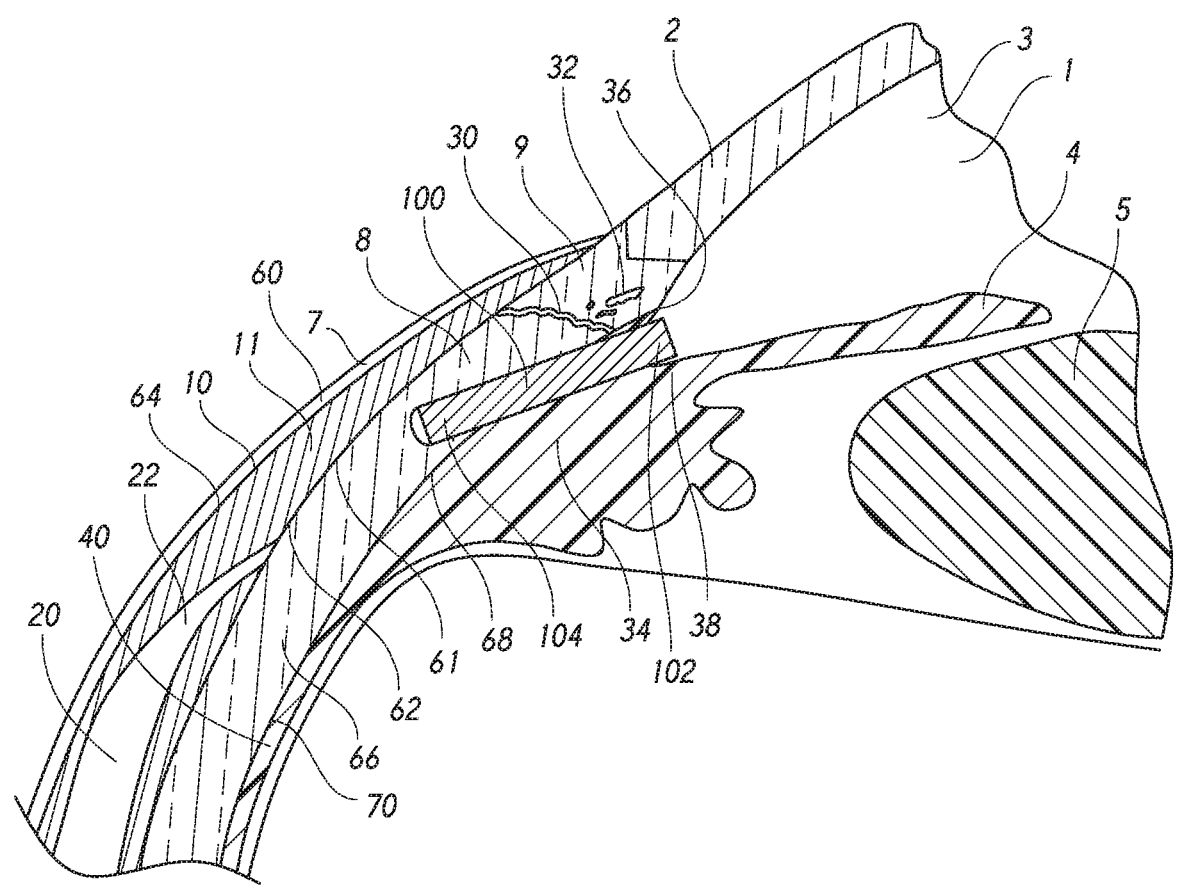
FIG. 1 is a cross-sectional diagram of the general anatomy of an eye and an intraocular implant therein.

In the following detailed description, numerous specific details are set forth to provide a full understanding of the subject technology. It should be understood that the subject technology may be practiced without some of these specific details. In other instances, well-known structures and techniques have not been shown in detail so as not to obscure the subject technology.

Further, while the present description sets forth specific details of various embodiments, it will be appreciated that the description is illustrative only and should not be construed in any way as limiting. Additionally, it is contemplated that although particular embodiments may be disclosed or shown in the context of ab externo procedures, such embodiments can be used in ab interno procedures. For example, although various ab externo approaches are discussed herein, any embodiment of the implant placement devices and methods described herein can be modified to provide an ab interno procedure (i.e. entering through the cornea, across the anterior chamber toward a target location) such that an outflow region of the shunt is positioned with the location of a bleb. Furthermore, various applications of such embodiments and modifications thereto, which may occur to those who are skilled in the art, are also encompassed by the general concepts described herein.

The present application discloses ab externo approaches and devices for positioning an intraocular implant with one end (e.g., a fluid entry end of a shunt) placed into a first region, such as the anterior chamber, and the other end placed preferably into a second region, such as the intrascleral space, without creating a conjunctival cutdown (dissection). Other possible second regions include the sub-Tenon's space (between Tenon's and sclera), the intra-Tenon's space (between layers of Tenon's capsule, or in the intra-Tenon's adhesion space), the over-Tenon's space (between Tenon's and conjunctiva), the choroidal and suprachoroidal space, the subconjunctival space, Schlemm's canal, the vitreous space, the episcleral vein, the supraciliary space, or the suprascleral space. Other possible first regions include the choroidal space or the vitreous space.

In some embodiments of the methods and devices disclosed herein, the implant injector can be configured to allow an intraocular shunt, such as a gel shunt (e.g., supported by a needle or shaft of the injector) to be positioned or oriented at a desired angle ("entrance angle") relative to a surface of the eye prior to implantation in order to allow the shunt outflow end to be positioned in a desired target outflow region, such as the intrascleral, suprachoroidal, or vitreous space. For example, the injector can be manually positionable relative to the surface of the eye to allow the surgeon to adjust the entrance angle to any of a variety of angles before injecting the shunt into the eye.

Additionally, according to some embodiments, an intraocular implant can be injected into any of the nasal quadrants of the eye using an ab externo procedure. For example, the intraocular implant can be injected in the nasal superior, nasal inferior, temporal superior, or temporal inferior quadrants.

Advantageously, using some embodiments of this procedure, an intraocular implant can be more easily placed in every quadrant of the eye because the injector needle no longer has to traverse the entire anterior chamber (compared to ab interno approaches). Thus, ab externo procedures are disclosed herein that enable a surgeon to quickly and accurately place a distal end of an intraocular implant into any quadrant of the eye and position a proximal end of the intraocular implant into one of a variety of regions without creating a scleral flap or conjunctival dissection.

FIG. 1 illustrates a detail view of an eye with an intraocular implant 100 therein. An anterior aspect of the anterior chamber 1 of the eye is the cornea 2, and a posterior aspect of the anterior chamber 1 of the eye is the iris 4. Beneath the iris 4 is the lens 5. The anterior chamber 1 is filled with aqueous humor 3. The aqueous humor 3 drains into a space(s) deep to the conjunctiva 7 through the trabecular meshwork of the sclera 8. The aqueous humor is drained from the space(s) deep to the conjunctiva 7 through a venous drainage system (not shown). FIG. 1 also illustrates a drug-eluting intraocular implant 100 having a distal or first portion 102 in the anterior chamber 1 and a proximal or second portion 104 in the intrascleral space 66.

As shown, the conjunctiva 7 attaches to the sclera 8 at the limbus 9. Deep to the conjunctiva 7 is Tenon's capsule 10. Tenon's capsule 10 comprises two layers (i.e., superficial and deep layers) and an intra-Tenon's adhesion space 11 that extends between the superficial and deep layers of Tenon's capsule 10. The intra-Tenon's adhesion space 11 surrounds the eye circumferentially. The intra-Tenon's adhesion space 11 can extend around the eye posterior to the limbus 9.

In the view of FIG. 1, deep to the intra-Tenon's adhesion space 11 is a rectus muscle 20. The eye has four rectus muscles (superior, inferior, lateral, and medial) that attach to sclera via a rectus tendon. FIG. 1 illustrates that the rectus muscle 20 attaches to the sclera 8 via a rectus tendon 22. For illustration purposes, the rectus tendon 22 is shown inserting onto the sclera 8. In some cases, there may not be a clear insertion point of the rectus tendon 22 onto the sclera 8, but there will be a gradual transition between the rectus tendon 22 and the intra-Tenon's adhesion space 11.

Additionally, as illustrated in FIG. 1, Tenon's capsule 10 and the intra-Tenon's adhesion space 11 is illustrated extending anteriorly relative to and superficial to the rectus muscle 20. As also shown, posterior to the rectus tendon, Tenon's capsule 10 and the intra-Tenon's adhesion space 11 also extend deep to and around the rectus muscle 20. In this region, there is a reflection of Tenon's capsule 10 and the intra-Tenon's adhesion space 11 from the rectus muscle 20 onto the globe or sclera 8. Thus, Tenon's capsule 10 and the intra-Tenon's adhesion space 11 envelop or encapsulate the rectus muscle 20.

FIG. 1 illustrates that in some locations, Tenon's capsule 10, and thus, the intra-Tenon's adhesion space 11, surrounds a rectus muscle 20. According to some embodiments of the methods disclosed herein, the intra-Tenon's adhesion space 11 can be accessed from the anterior chamber 1. Tenon's capsule 10 and the intra-Tenon's adhesion space 11 surround the eye circumferentially.

FIG. 1 also illustrates the drainage channels of the eye, including Schlemm's canal 30 and the trabecular meshwork 32, which extend through the sclera 8. Further, deep to the sclera 8, the ciliary body 34 is also shown. The ciliary body 34 transitions posteriorly to the choroid 40. Deep to the limbus 9 is a scleral spur 36. The scleral spur 36 extends circumferentially within the anterior chamber 1 of the eye. Further, the scleral spur 36 is disposed anteriorly to the anterior chamber angle 38. Furthermore, "anterior chamber angle tissue" can refer to the eye tissue in the region extending along and/or including one or more of the cornea 2, the sclera 8, Schlemm's canal 30, the trabecular meshwork 32, the ciliary body 34, the iris 4, or the scleral spur 36.

Accordingly, for definitional purposes, the space between the conjunctiva 7 and Tenon's capsule 10 or the intra-Tenon's adhesion space 11 is referred to herein as subconjunctival space 60 (here shown as a potential space). The space between the sclera 8 and Tenon's capsule 10 or the intra-Tenon's adhesion space 11 is referred to herein as suprascleral space 61 (here shown as a potential space). Further, the space between a deep layer or surface 62 and a superficial layer or surface 64 of Tenon's capsule 10 is referred to herein as the intra-Tenon's adhesion space 11. Additionally, the space within the sclera 8 (i.e., between the superficial and deep layers or surfaces of the sclera 8) is referred to herein as intrascleral space 66 (here shown as a potential space). The space between the sclera 8 and the ciliary body 34 is referred to herein as supraciliary space 68 (here shown as a potential space). Finally, the space between the sclera 8 and the choroid 40 is referred to as suprachoroidal space 70 (here shown as a potential space). The supraciliary space 68 can be continuous with the suprachoroidal space 70.

FIGS. 2-6 illustrate various embodiments of a drug-eluting intraocular implant 100. Although embodiments are described herein as drug-eluting, a drug-eluting intraocular implant 100 can comprise one or more pharmaceutical and/or biological agents, e.g., drugs, biologics, pharmaceuticals, and/or other chemicals. For example, a drug can be selected to regulate the body's response to the implantation of the implant and a subsequent healing process. The drug can be carried by the intraocular implant 100 for eluting or delivery to target location(s).

In some embodiments, the intraocular implant 100 can comprise one or multiple drug-eluting portions, which can each be formed to provide different dissolving times and/or have different drugs embedded therein. Accordingly, in some embodiments, two or more drugs can be delivered simultaneously on independent release timings. For example, a drug can be integrated into only one of the ends of the intraocular implant 100 to provide a single drug-eluting end which can be placed into the anterior chamber or location of lower pressure. For example, a first portion or a first end can be drug-eluting. Further, other than being formed along an end of the intraocular implant, the drug-eluting portion can also be formed along an intermediate portion of the intraocular implant. Accordingly, embodiments can provide a targeted drug release inside the anterior chamber, inside the sclera, and/or in the subconjunctival space or other target location, depending on the location and configuration of the drug-eluting portion(s).

The intraocular implant 100 can be impregnated, packed, or coated with a drug. In some embodiments, the drug may coat and/or impregnate an entire exterior of an intraocular implant, an entire interior of the intraocular implant, or both. Alternatively, a drug may coat and/or impregnate a portion of an exterior of the intraocular implant, a portion of an interior of the intraocular implant, or both. In some embodiments in which the drug is impregnated into the intraocular implant 100, the intraocular implant itself can be partially or completely dissolvable. By including the biologics, pharmaceuticals, drugs, or other chemicals in the liquid gelatin, the formed intraocular implant will be impregnated with the biologics, pharmaceuticals, drugs, or other chemicals. In some embodiments, a time-release or controlled-release drug can be provided by means of an impregnated portion or coating to provide a desired dissolution rate. Such drug-eluting portion(s) of the intraocular implant can provide a drug delivery, even without aqueous flow.

FIGS. 2-6 illustrate embodiments of an intraocular implant 100 having an elongate body with a first end 106 and a second end 108 opposite the first end 106. The length of the intraocular implant 100 between the first and second ends 106, 108 can be any length sufficient to provide a quantity of drug or a passageway between a target location of a first portion 102 of the implant and a target location of a second portion 104 of the implant. For example, a length of the intraocular implant 100 may be selected so that the first portion 102 is within the anterior chamber 1, and the second portion 104 is within the intrascleral space 66. In some embodiments, the length of the intraocular implant 100 is selected so that the first portion 102 is not visible to the patient. For example, the length can be selected so that the first portion 102 does not extend into the anterior chamber 1. Preferably, the first portion 102 does not extend more than 4 mm into the anterior chamber 1. Typically, the length of the intraocular implant 100 is between approximately 2 to 8 mm with a total length of approximately 6 mm, in most cases being preferred.

The diameter of the outer surface of the intraocular implant 100 can be any diameter that permits the implant to be retained and deployed from an implant injector needle. Accordingly, the outer diameter of the intraocular implant 100 corresponds to an inner diameter, or gauge, of the needle. In some embodiments, a 30 gauge needle having a thin wall is used. In a preferred embodiment, a 27 gauge needle is used with an intraocular implant 100 that can have an outer diameter of approximately 250-260 micrometers. In some embodiments, a 25 gauge needle is used with an intraocular implant 100 that can have an outer diameter of approximately 300-350 micrometers. In some embodiments, a 23 gauge needle is used. In some embodiments, a 20 gauge needle is used with an intraocular implant 100 that can have an outer diameter of approximately 600-700 micrometers.

The intraocular implant 100 can comprise one or more rigid and/or flexible materials. For example, the implant can comprise a soft biocompatible material, such as a soft polymer material and/or a gelatin material. Further, in some embodiments, the body of the intraocular implant 100 can comprise only a resilient or flexible material, such as a gelatin or another similar material. In some embodiments, the intraocular implant 100 can comprise only a rigid material, such as steel or another similar material. In some embodiments, the intraocular implant 100 can comprise a combination of materials. For example, the intraocular implant 100 can comprise a rigid material having a portion coated with a flexible material.

The flexible material is less erosive to eye tissue surrounding or engaged against the implant. The flexible material can also reduce and/or avoid degradation and or irritation to the eye. Further, the material of the intraocular implant can be capable of swelling or expanding. When the material swells or expands within the eye, the intraocular implant can be secured or anchored within the eye, thus reducing the likelihood of movement or implant migration within the eye. In some embodiments, the implant 100 or at least a portion of the outer surface of the intraocular implant 100 may swell within the intrascleral space 66, thus reducing migration of the intraocular implant 100 toward the interior chamber 1. For example, the implant 100 can comprise a swellable polymer or gelatin material that enables the implant to expand within the eye after implantation, thereby tending to engage and anchor the implant within the eye relative to the sclera.

The intraocular implant 100 can be a rigid material having a portion of an outer surface coated with a flexible material that can expand within the eye to restrict movement or migration of the implant. In another aspect, the intraocular implant 100 can comprise only the flexible material.

The intraocular implant 100 can be partially or completely dissolvable as the drug is released or eluted. In some embodiments, the intraocular implant 100 reduces in size as the drug is released into the eye. In some embodiments, the drug releases from a portion of the intraocular implant 100, such as the first and/or the second portion 102, 104. In some embodiments, a length of the intraocular implant 100 reduces as the drug releases from a portion or an end of the body. In some embodiments, the drug releases along a gradient so that more of the drug is released at a portion or an end of the intraocular implant relative to another portion or end of the intraocular implant.

In some embodiments, the flexible material selected for the intraocular implant 100 can be a gelatin or other similar material. For example, a gelatin used for making the implant can be a gelatin Type B from bovine skin. A preferred gelatin is PB Leiner gelatin from bovine skin, Type B, 225 Bloom, USP. Another material that may be used in the making of the implant is a gelatin Type A from porcine skin, also available from Sigma Chemical. Such gelatin is available is available from Sigma Chemical Company of St. Louis, Mo. under Code G-9382. Still other suitable gelatins include bovine bone gelatin, porcine bone gelatin and human-derived gelatins. In addition to gelatins, microfistula implant may be made of hydroxypropyl methycellulose (HPMC), collagen, polylactic acid, polyglycolic acid, hyaluronic acid and glycosaminoglycans.

If a gelatin implant is used, the delivery of the implant can be performed by wetting an inside the needle of the intraocular implant injector with a balanced salt solution (e.g., Dulbecco's Phosphate Buffered Saline), a steroid, or other drug prior to implantation. Such priming ensures that the implant remains flexible before implantation. Further, an amount of a basic salt solution (BSS), a viscoelastic, an antimetabolite, a drug-eluting solution, water, and/or a combination thereof can be optionally injected through the needle, and in some embodiments, through the implant, into a target space to create a primed space for outflow and to deliver a drug, such as an antifibrotic to that new drainage space.

The intraocular implant 100 material can be cross-linked. For example, when a gelatin is used, cross-linking can increase the inter- and intramolecular binding of the gelatin substrate. Any means for cross-linking the gelatin may be used. In some embodiments, the formed gelatin implants can be treated with a solution of a cross-linking agent such as, but not limited to, glutaraldehyde. Other suitable compounds for cross-linking include 1-ethyl-3-(3-dimethylaminoproply)carbodiimide (EDC). Cross-linking by radiation, such as gamma or electron beam (e-beam) may be alternatively employed.

Aspects related to embodiments of drug delivery implants are discussed in co-pending U.S. Patent Application Publication No. 2012/0197175, filed on Dec. 8, 2008, U.S. Patent Application Publication No. 2014/0236066, filed on Feb. 19, 2013, the entireties of each of which is incorporated herein by reference.

FIG. 2 illustrates an embodiment of an intraocular implant 100 having a cylindrical shaped body with a solid cross-section between a portion of the length between a first end 106 and a second end 108. The intraocular implant 100 can comprise a rigid material, a resilient or flexible material, or any combination thereof. For example, the cylindrical shaped body can be a rigid material such as surgical steal coated with a flexible material to reduce and/or avoid erosion of the eye or migration of the implant. In some embodiments, the intraocular implant 100 can be entirely comprised a flexible material such as a gelatin. In some embodiments, the flexible material can be impregnated with a drug configured to be eluted from the intraocular implant 100 to the eye.

FIG. 3 illustrates an embodiment of an intraocular implant 100 having a cylindrical shaped body with a hollow cross-section between a portion of the length between a first end 106 and a second end 108. In some embodiments, an inner surface of the implant defines a cavity that can retain a drug. In some embodiments, a passage 110 extends through the outer surface and is in fluid communication with the cavity. The intraocular implant 100 can have a first passage 110 extending through a first end 106 of a first portion 102, and a second passage extending through a second end 108 of a second portion 104 to define a flow path between the first and second ends 106, 108. The first end 106 can receive fluid into the flow path from an anterior chamber of an eye and the second end 108 can direct the fluid to a location of lower pressure with respect to the anterior chamber 1. Some locations of lower pressure include the intrascleral space, intra-Tenon's space, the subconjunctival space, the episcleral vein, the subarachnoid space, and Schlemm's canal.

In some embodiments, the passage extends through an outer surface of the body, between the first and second ends 106, 108. For example, the passage can be an aperture or slit through the first and/or second portions 102, 104.

In some embodiments, the inner diameter and/or the length of the intraocular implant 100 can be varied in order to regulate the flow rate through implant. In some embodiments, the inner surface of the implant defines a variable inner diameter that increases along the length between the first and second ends 106, 108. In some embodiments, the inner diameter continuously increases along the length of the implant. In some embodiments, the inner diameter remains constant along portions of the length of the implant.

In some embodiments, the cavity of the intraocular implant 100 can packed, plugged, or filled with a drug to be eluted to the eye. In some embodiments, the cavity is coated with the drug to form a flow path or lumen. The drug can then be eluted into a fluid that enters the flow path of the cavity. As the drug is eluted, the lumen can become enlarge and the surface area of the drug that interacts with the fluid flow can increase. In some embodiments, the intraocular implant 100 is a shunt that comprises a flow path through the first and second ends 106, 108 and the cavity. IN an example, a cross-section of the cavity can be entirely filled with a drug so that no flow is permitted through cavity. In another example, the cavity can be filled with a drug so that after the drug begins to elude a flow path opens and flow through both the first and second ends 106, 108 is permitted like a shunt. In some embodiments, the cavity can be coated with a drug so that a flow path is formed and the intraocular implant 100 functions as shunt to permit a fluid flow through the first and second ends 106, 108.

Still referring to FIG. 3, the intraocular implant 100 can comprise a rigid material, a flexible material, or any combination thereof. For example, a rigid material can define a cylindrical shape body having one or more passage. In some embodiments, all or a portion of the rigid material such as surgical steal is coated with a resilient or flexible material to reduce and/or avoid erosion of the eye or migration of the implant. In some embodiments, the intraocular implant 100 can be entirely comprised a flexible material such as a gelatin. In some embodiments, the flexible material can be impregnated with a drug configured to be eluted from the intraocular implant 100 to the eye.

Referring to FIG. 4, an embodiment of an intraocular implant 100 is illustrated having an outer surface with a more than one cross-sectional width. The intraocular implant 100 can have a first portion 102 proximate to a first end 106, and a second portion 104 proximate to a second end 108 opposing the first end 106. The second portion 104 can have a cross-sectional width that is greater than the first portion 102. For example, the outer surface of the intraocular implant 100 can have a cross-sectional width that tapers from the second portion 104 toward the first portion 102. Further, the outer surface can taper at a consistent slope between the first and second portions. In some embodiments, the outer surface can comprise one or more ridges or steps so that a cross-sectional width of the outer surface is greater at the second portion 104 than the first portion 102.

The tapered outer surface can reduce and/or prevent movement or migration of the intraocular implant 100 within the eye. For example when the intraocular implant 100 is positioned within an eye so that the first portion 102 is positioned within the interior chamber 1 and the second portion 104 is within the intrascleral space 66, the second portion 104 is held or retained within intrascleral space 66 and movement of the intraocular implant 100 toward the interior chamber 1 is reduced and/or avoided.

In some embodiments, a portion of the intraocular implant 100 can be coated, layered, and/or impregnated with one or more drugs that can be eluted from the implant. In some embodiments, the intraocular implant 100 comprises one or more passage in fluid communication with a cavity. The cavity can be filled or coated with a drug such that the drug is released from a passage. In some embodiments, the intraocular implant 100 comprises a flow path or lumen extending through a first portion 102 and/or second portion 104, the drug being eluted to a fluid permitted through the flow path.

As noted above, the methods can be performed to provide treatment with a drug or pharmaceutical, such as by implanting an intraocular implant that has been coated, layered, packed, and/or impregnated with a pharmaceutical and/or biological agent, by treating the eye topically with a pharmaceutical and/or biological agent, and/or by injecting a pharmaceutical and/or biological agent into the anterior chamber and/or a target outflow region, including any target outflow regions discussed or referenced herein, prior to or after releasing a implant from the device. Suitable agents that can be used in some embodiments disclosed herein may include, for example, any of those disclosed in the following U.S. Pat. Nos. 8,785,394; 8,062,657; 7,799,336; 7,790,183; 7,033,605; 6,719,991; 6,558,686; 6,162,487; 5,902,283; 5,853,745; and 5,624,704; and U.S. Patent Publication No. 2008/0108933; the content of each of these references is incorporated by reference herein its entirety. Examples of suitable agents include antimitotic pharmaceuticals such as Mitomycin-C or 5-Fluorouracil, anti-VEGF (such as Lucintes, Macugen, Avastin, VEGF or steroids), anticoagulants, antimetabolites, angiogenesis inhibitors, steroids, anti-inflammatories, antibiotics, antiseptics, disinfectants, brimonidine, timolol, prostaglandin analogs (such as travoprost, latanoprost, and tafluprost), prostamides (such as bimatoprost), cyclosporin, pilocarpine, corticosteroids and other steroid derivatives (such as hydrocortisone, dexamethasone, beclomethasone dipropionate, triamcinolone, triamcinolone acetate, cortisol benzoate), or other agents or combinations thereof, for treating conditions of the eye, such as glaucoma, dry eye, allergy, or conjunctivitis, to name a few. Additional agents are provided further below.

Referring to FIG. 5, an embodiment of an intraocular implant 100 is illustrated comprising one or more protrusion 112 extending from an outer surface to reduce and/or avoid movement or migration of the intraocular implant 100 within the eye. The protrusion 112 can be a convex or concave portion of the outer surface of the intraocular implant 100. In an example, the protrusion 112 is a portion of the outer surface of the implant that extends outward from a longitudinal axis of the implant. In some embodiments, the protrusion 112 can comprise a barb, a ridge, a lip, or other similar features configured to engage a portion of the eye and reduce and/or avoid movement of the intraocular implant 100 within the eye.

In some embodiments, the intraocular implant 100 comprises a protrusion 112 extending from the outer surface of a second portion 104 to reduce and/or avoid movement toward the anterior chamber of the eye. For example, when the intraocular implant 100 is positioned within an eye so that the first portion 102 is positioned within the interior chamber 1 and the second portion 104 is within the intrascleral space 66, movement of the intraocular implant 100 toward the interior chamber 1 is reduced and/or avoided by engagement of the protrusion 112 against the sclera or other eye tissue. In some embodiments, the intraocular implant 100 comprises protrusions 112 extending from the outer surface at the first and second portions 102, 104.

FIG. 6 illustrates an embodiment of an intraocular implant 100 comprising a cylindrically shaped housing having a first end 106, a second end 108 opposite the first end 106, and an inner surface defining a cavity 114. A first end 106 comprises an opening defining a passage 110 extending from the outer surface to the cavity 114. In some embodiments, the cavity 114 comprises a drug 116 configured to be released through the passage 110. In some embodiments, the passage comprises a membrane 118, a mesh material, or other similar material that permits a fluid or a drug to move through the passage at a specified rate. In some embodiments, the passage 110 is a portion of the intraocular implant 100 comprising a porous material.

The intraocular implant 100 can comprise an elongate body 120 having a coating 122 on an outer surface. The coating 122 can be a flexible material to reduce and/or avoid movement and/or erosion to the surrounding eye tissue. In some embodiments, the coating 122 is impregnated with a drug to regulate the body's response to the implantation of the implant and the subsequent healing process.

As used herein, "controlled release" or "time-release" may refer to the release of an agent such as a drug from a composition or dosage form in which the agent is released according to a desired profile over an extended period of time. For example, such release can effect delivery of an active over an extended period of time, defined herein as being between about 60 minutes and about 2, 4, 6, 8 or even 12 hours. Controlled release profiles may include, for example, sustained release, prolonged release, pulsatile release, and delayed release profiles. Controlled release may also be defined functionally as the release of over 80 to 90 percent (%) of the active ingredient after about 60 minutes and about 2, 4, 6 or even 8 hours. Controlled release may also be defined as making the active ingredient available to the patient or subject regardless of uptake, as some actives may never be absorbed by the animal.

In contrast to immediate release compositions, controlled release compositions may permit delivery of an agent to a subject over an extended period of time according to a predetermined profile. Such release rates can provide therapeutically effective levels of agent for an extended period of time and thereby provide a longer period of pharmacologic or diagnostic response as compared to conventional rapid release dosage forms. Such longer periods of response may provide many benefits that are not achieved with the corresponding short acting, immediate release preparations.

In accordance with some embodiments, a variety of injectors or systems known in the art may be used to perform the methods disclosed herein. In some embodiments, deployment into the eye of an intraocular implant 100 can be achieved using a hollow needle or shaft configured to hold the implant, as described herein. The needle can be coupled to an injector or be a part of the injector itself. Some of the methods disclosed herein enable a surgeon to use an injector in a "freehand" procedure (i.e., without using docking, securement, or coupling devices) to inject an implant into the eye. However, some of the methods disclosed herein also enable a surgeon to use a "guiding" injector placement device. Optionally, the placement device can be temporarily affixed or secured to the eye or to the inserter itself during the procedure. Such injector placement devices can be retrofitted to existing injectors or incorporated into injector designs.

Some injectors that are suitable for placing shunts according to some embodiments include, but are not limited to, injectors described in U.S. Pat. Nos. 6,007,511, 6,544,249, U.S. Patent Publication No. 2008/0108933, U.S. Pat. No. 8,663,303, U.S. Patent Application Publication No. 2012/0123434, filed on Nov. 15, 2010, U.S. Pat. No. 8,721,702, filed on Nov. 15, 2010, U.S. Pat. No. 9,585,790, filed on Nov. 13, 2014, and U.S. Patent Application No. 62/170,338, filed on Jun. 3, 2015, the entire contents of each of which is incorporated by reference herein.

Furthermore, in accordance with some embodiments, the injector can use one, two, or more actuation mechanisms, including buttons, sliders, rotational components, and combinations thereof. For example, an injector can be configured to include two buttons, a button and a slider, two sliders, and/or rotational components. The advancement or withdrawal of a component of the injector (such as a plunger rod, needle, sleeve, or other component) can be done either through actuation of a button and/or a slider, and may be manual or use an energy stored mechanism (e.g., spring loaded actuation, electrical motor, or magnetic movement).

A drug-eluting intraocular implant implementing any of the features discussed or referenced herein can be implanted into any area of the eye to achieve release of a drug to a target area, and in some instances, create a fluid flow path from a target area. For example, the implant can be deployed with a distal or first end in the anterior chamber, and a proximal or second end in the intrascleral space, with the ability to deliver drugs at either or both ends or along an intermediate portion thereof. Some methods can be implemented such that multiple implants, with the same or different drugs and with the same or different release timings, can be implanted in different places (e.g., the subconjunctival space, the suprachoroidal space, the anterior chamber, etc.). Other methods and procedures can be performed to incorporate any of the implants discussed or referenced herein. Further, additional procedures for delivering drug-eluting plugs or shunts within the eye can be performed using one or more of the systems or devices disclosed herein. For example, the present disclosure can be used in combination with any of the shunts, plugs, or methods disclosed in U.S. Patent Application Publication No. 2016/0354244, filed on Jun. 2, 2016, and U.S. Patent Application Publication No. 2016/0354245, filed on Jun. 2, 2016, the entirety of each of which is incorporated herein by reference.

Figure 7:
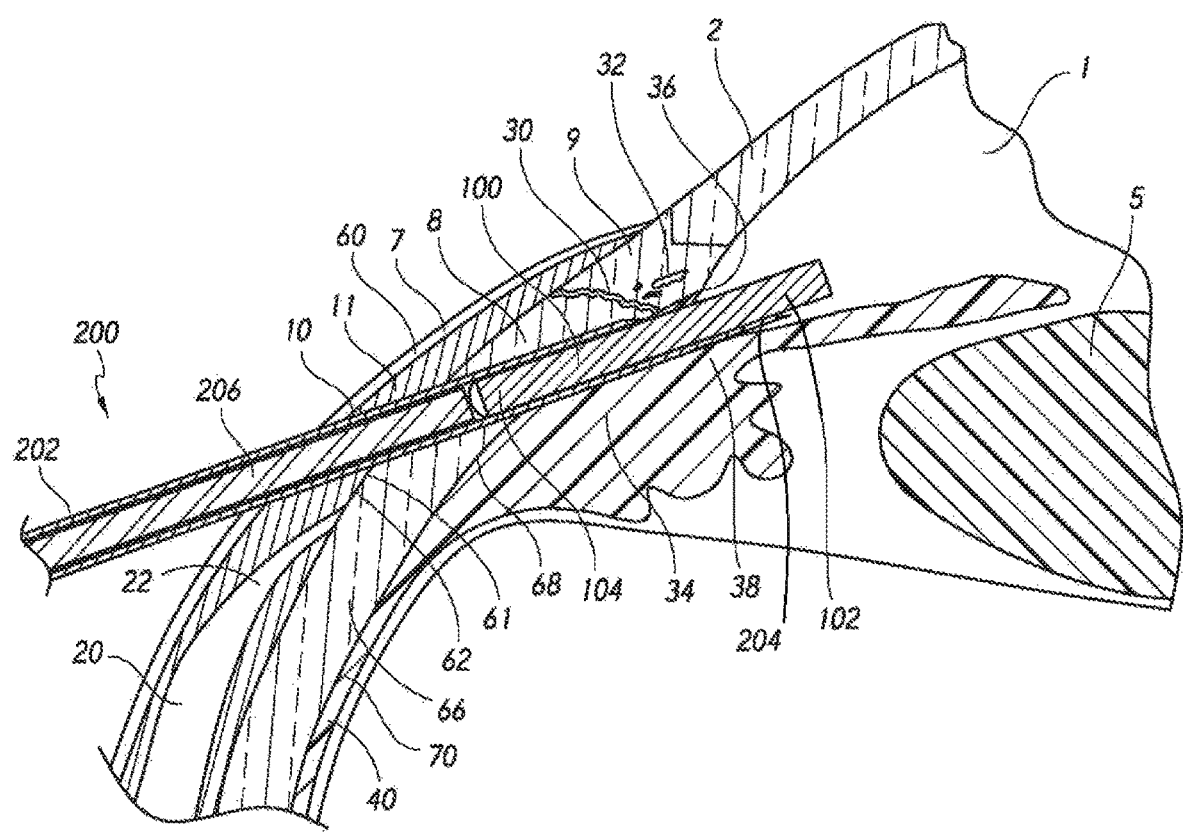
FIGS. 7-10 illustrate a procedure for placing an intraocular implant into an eye using an implant injector, according to some embodiments.

FIGS. 7-10 illustrate steps of a procedure for ab externo implantation of an intraocular implant, according to some embodiments. FIG. 7 illustrates an initial step of ab externo insertion of a needle of an implant injector 200 into an eye. The needle 202 can be configured to retain an intraocular implant 100. In some embodiments, the intraocular implant 100 is positioned within a portion of the needle proximal to a distal end 204. The intraocular implant 100 can be retained proximal to the distal end 204 by a pusher rod 206 retained within the needle.

To insert the intraocular implant in an eye, the needle 202 is advanced into the eye to pierce the conjunctiva 7, the Tenon capsule 10, and the sclera 8. In some instances, as the needle penetrates the eye and is advanced through the conjunctiva 7 toward the anterior chamber 1, the conjunctiva 7 and the Tenon capsule 10 are pushed down or compressed toward the sclera 8.

The intraocular implant 100 and the pusher rod 206 may travel forward with the needle 202. For example, as shown in FIG. 7, the intraocular implant 100 and the pusher rod 206 may travel forward with the needle 202 and penetrate conjunctiva 7, the Tenon capsule 10, and the sclera 8 of the eye until reaching a target or final position for the intraocular implant 100. In some embodiments, the intraocular implant 100 is in a final position when a distal portion of the implant (e.g., first portion 102) is within the anterior chamber 1, and a proximal portion of the implant (e.g., second portion 104) is within the intrascleral space 66. In some embodiments, the intraocular implant 100 is in a final position when the first portion 102 extends 0.2-0.4 mm into the anterior chamber 1. Preferably, the intraocular implant 100 is in a final position when the second portion 104 is within the intrascleral space 66 and a second end 108 of the implant does not extend into the subconjunctival space 60 or the suprascleral space 61. In some embodiments, a distal portion of the implant (e.g., first portion 102) is positioned in a choroidal space or a vitreous space in a final position.

Figure 8:
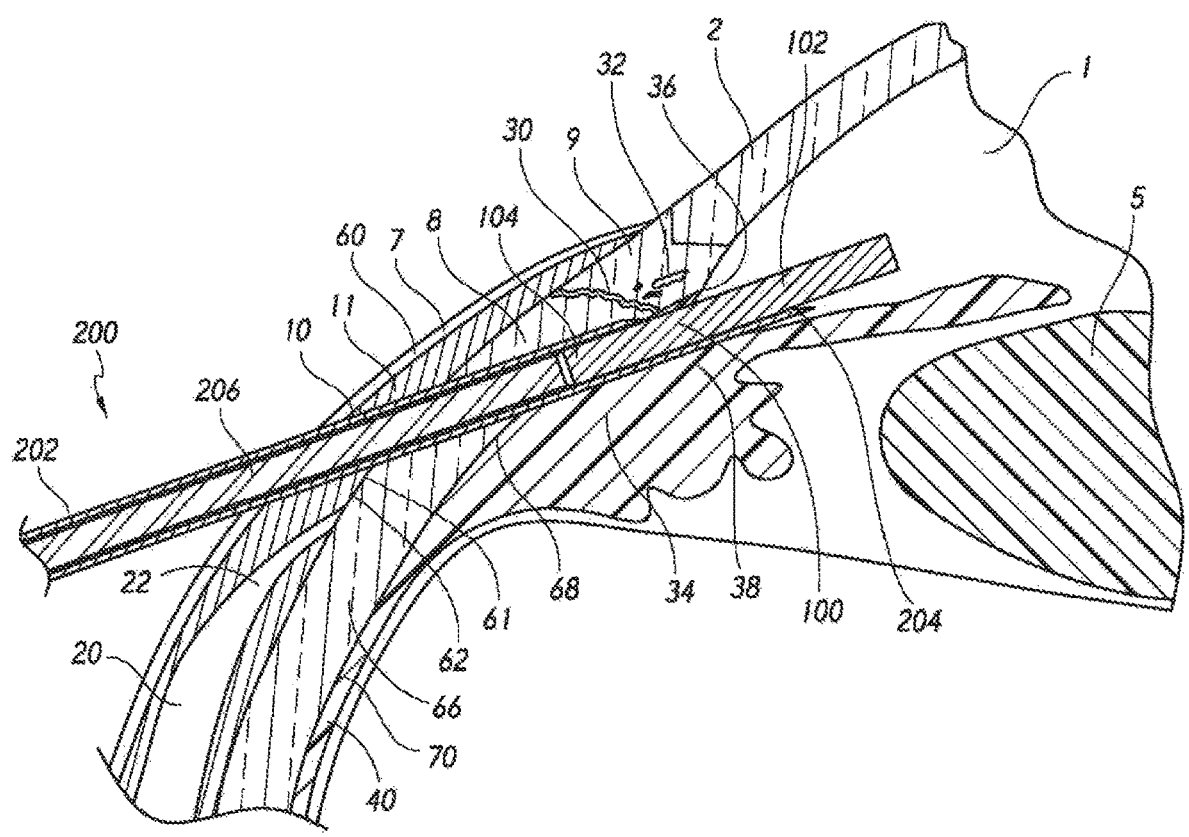

In some embodiments where the intraocular implant 100 is not positioned proximal to a distal end 204 of the needle 202 during or after advancement of the injector 200 into the eye, the implant can be advanced by the actuation of the pusher rod 206 until reaching a position as illustrated in FIG. 8.

Figure 9:
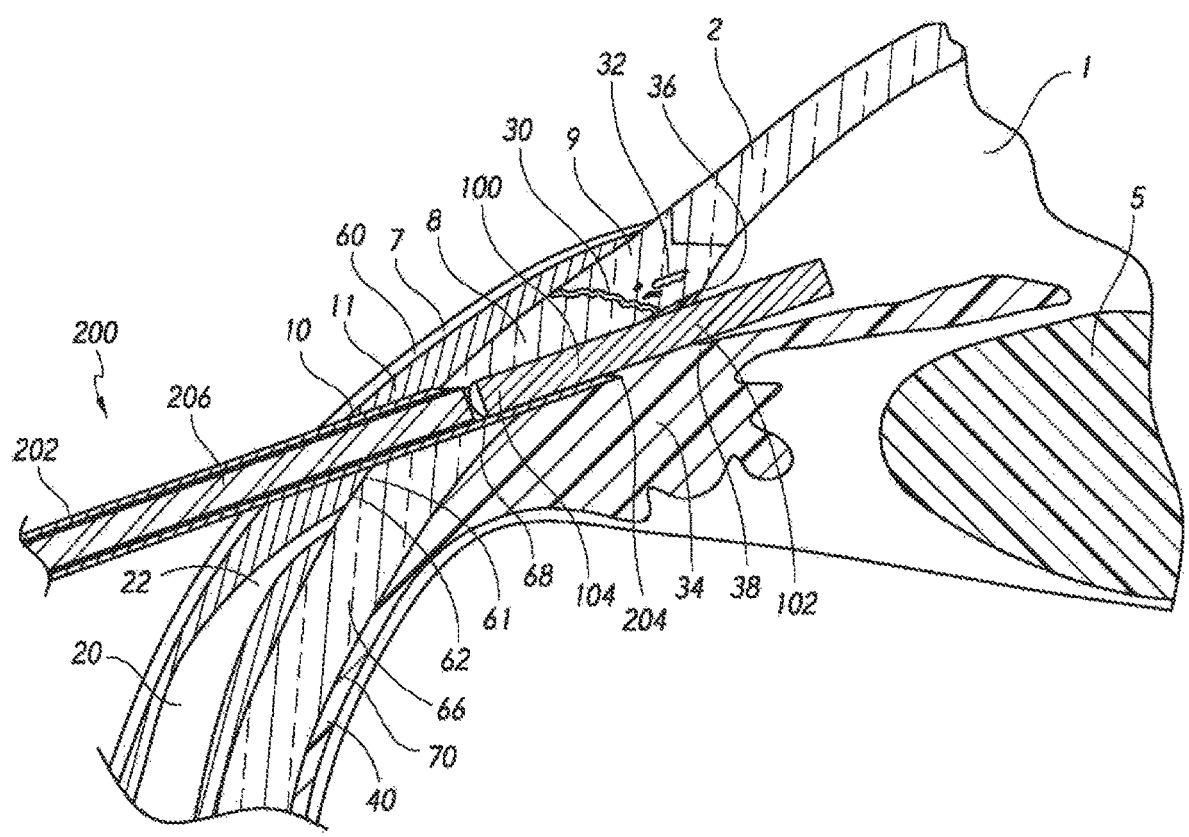
Figure 10:
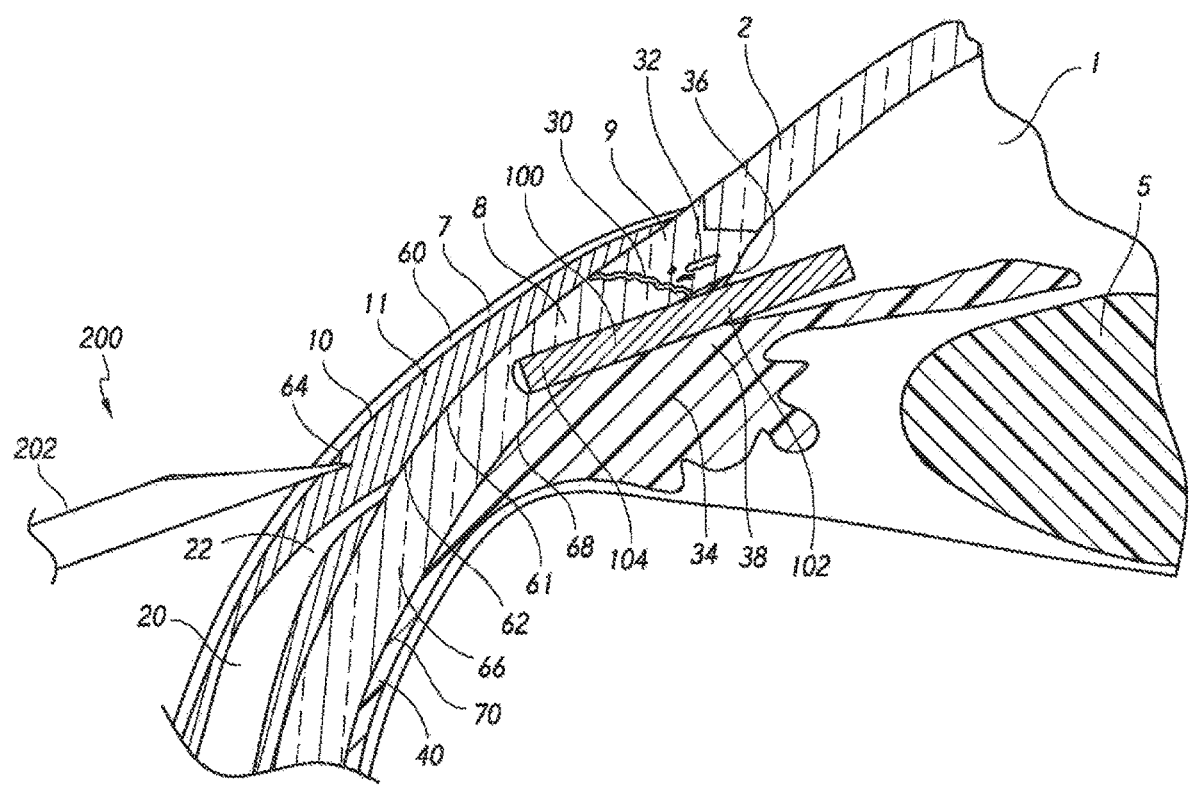

Referring to FIG. 9, once the intraocular implant 100 is in its final position, the needle 202 can be partially retracted while position of intraocular implant 100 is maintained by the pusher rod 206. In some embodiments, the position of intraocular implant 100 can be maintained by the pusher rod 206 until the distal end 204 of the needle 202 is proximally of the second portion 104 of the implant. Once the needle 202 is near the second portion 104 of the implant, the pusher rod 206 can be retracted and the needle 202 withdrawn, as shown in FIG. 10.

Figure 11:
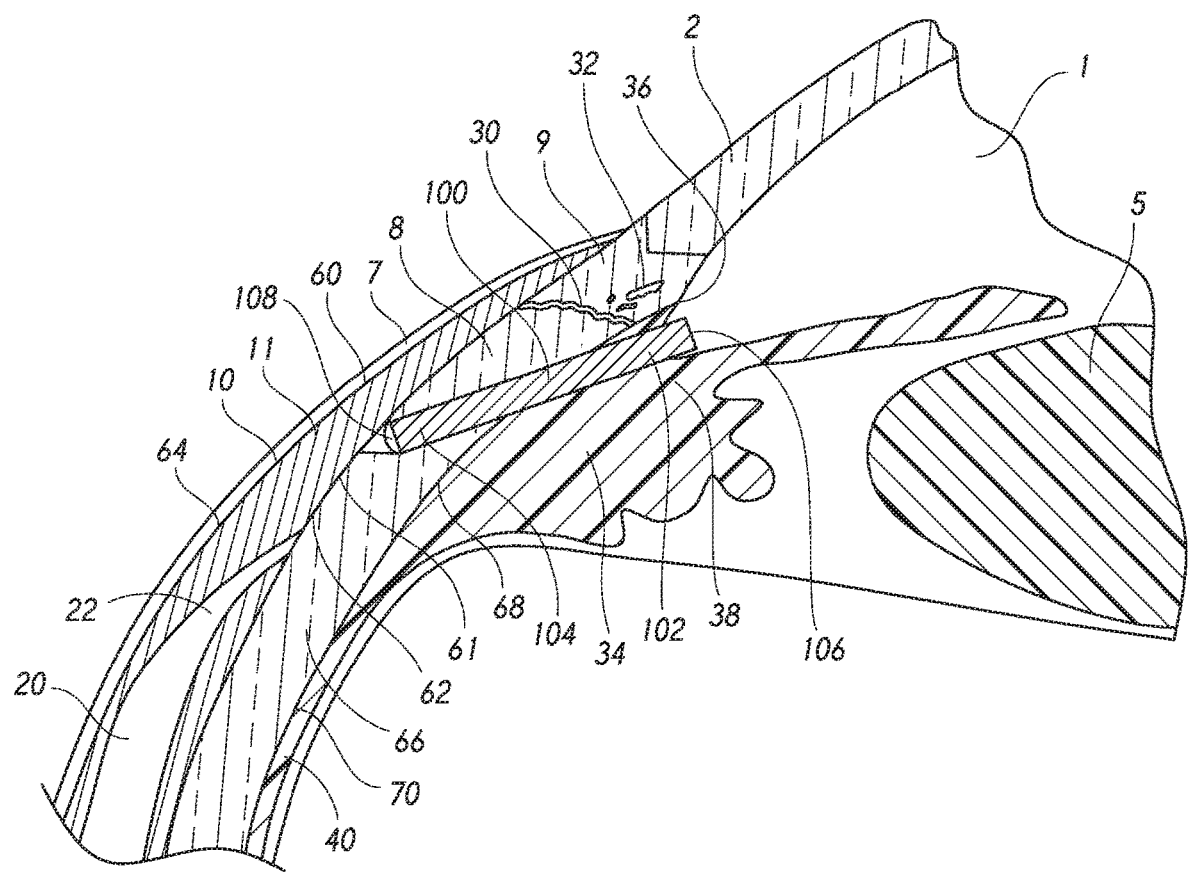
FIGS. 11-13 illustrate an intraocular implant positioned in the intrascleral space of an eye, according to some embodiments.
Figure 12:
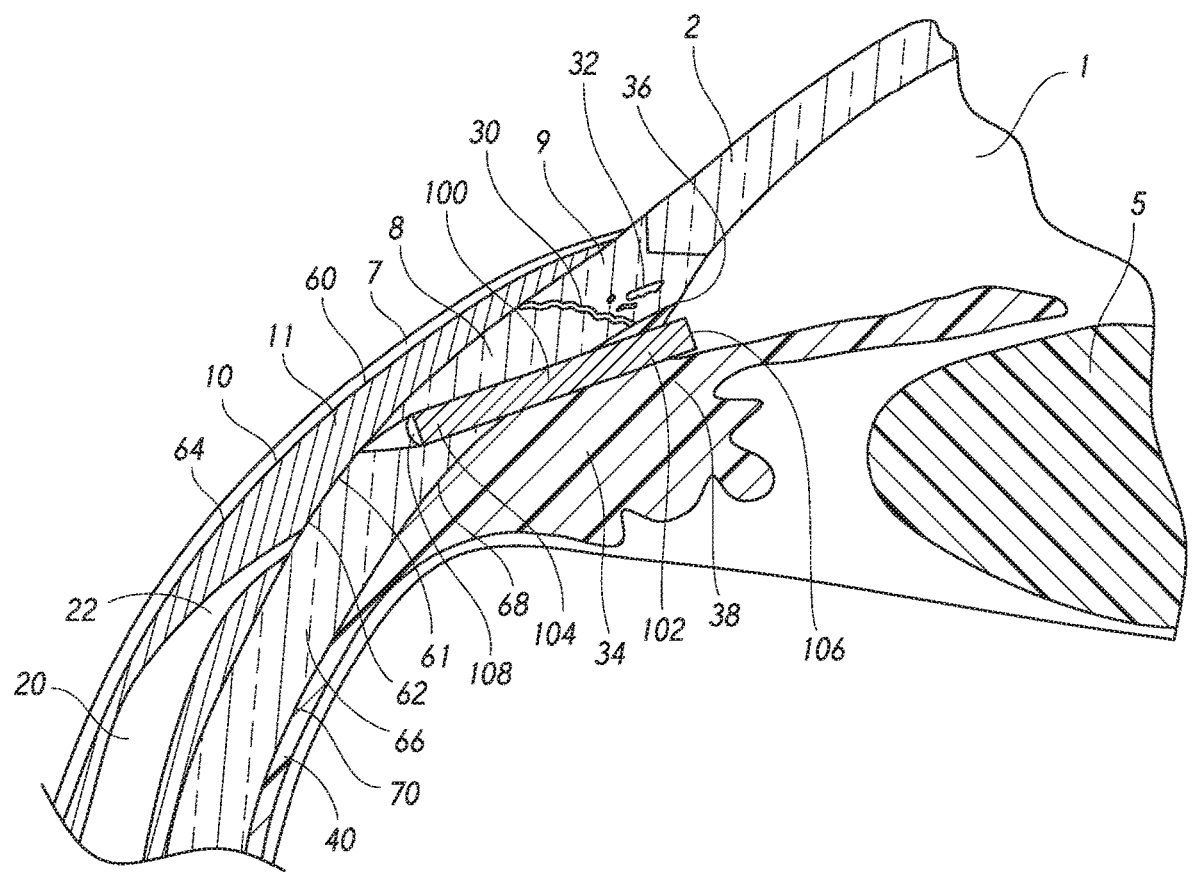
Figure 13:
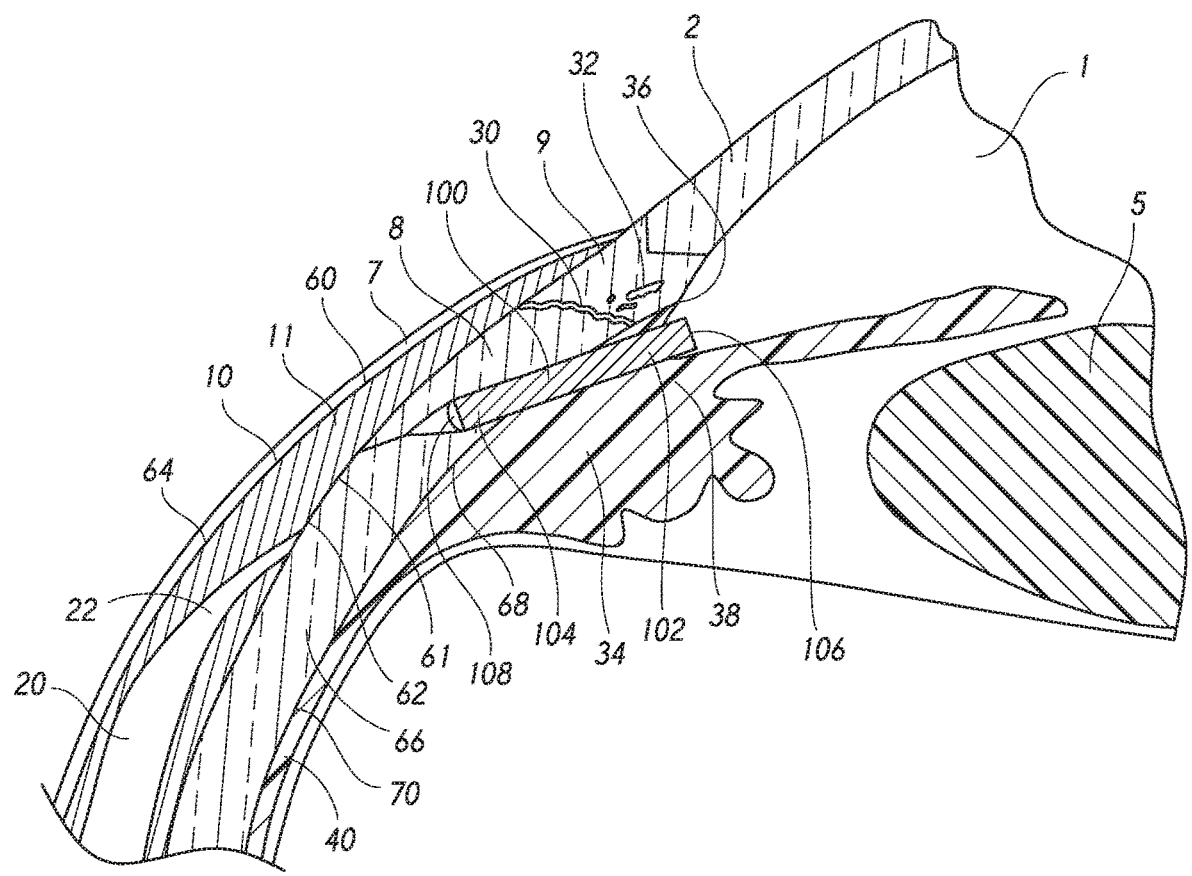

FIGS. 11-13 illustrate aspects of a final position of the intraocular implant 100 having a second portion 104 positioned within the intrascleral space 66. FIG. 11 illustrates the intraocular implant 100 with a first end 106 within the anterior chamber 1, and a second end 108 aligned with a superficial wall of the sclera 8. In this embodiment, the portion of the sclera 8 pierced by the needle may not heal (e.g., remain separated). In some embodiments, the final position of the intraocular implant 100 illustrated in FIG. 11 permits a drug to be released from the second portion 104 of the implant toward the subconjunctival space 60 or the suprascleral space 61. In some embodiments, the final position of the intraocular implant 100 illustrated in FIG. 11 permits a fluid flow through the implant.

FIG. 12 illustrates the intraocular implant 100 with a first end 106 within the anterior chamber 1, and a second end 108 spaced from the superficial wall of the sclera 8 by approximately 0.25-0.5 mm. In this embodiment, opposing surfaces of the portion of the sclera 8 pierced by the needle 202 can move toward each other and may heal. In some embodiments, the final position of the intraocular implant 100 illustrated in FIG. 12 permits a drug to be released from the second portion 104 of the implant and through the portion of the sclera 8 pierced by the needle 202 toward the subconjunctival space 60 or the suprascleral space 61. In some embodiments, the portion of the sclera 8 pierced by the needle 202 permits a fluid flow through the implant and/or regulated flow permitted through implant.

FIG. 13 illustrates the intraocular implant 100 with a first end 106 within the anterior chamber 1, and a second end 108 spaced from the superficial wall of the sclera 8 by approximately 0.75 mm. In this embodiment, opposing surfaces of the portion of the sclera 8 pierced by the needle 202 can move toward each other and permit the sclera to heal. In some embodiments, the final position of the intraocular implant 100 illustrated in FIG. 1 permits a drug to be released from the second portion 104 of the implant and through the portion of the sclera 8 pierced by the needle 202 toward the subconjunctival space 60 or the suprascleral space 61. In some embodiments, the portion of the sclera 8 pierced by the needle 202 does not permit a fluid flow through implant or portion of the sclera 8 pierced by the needle 202.

Figure 14:
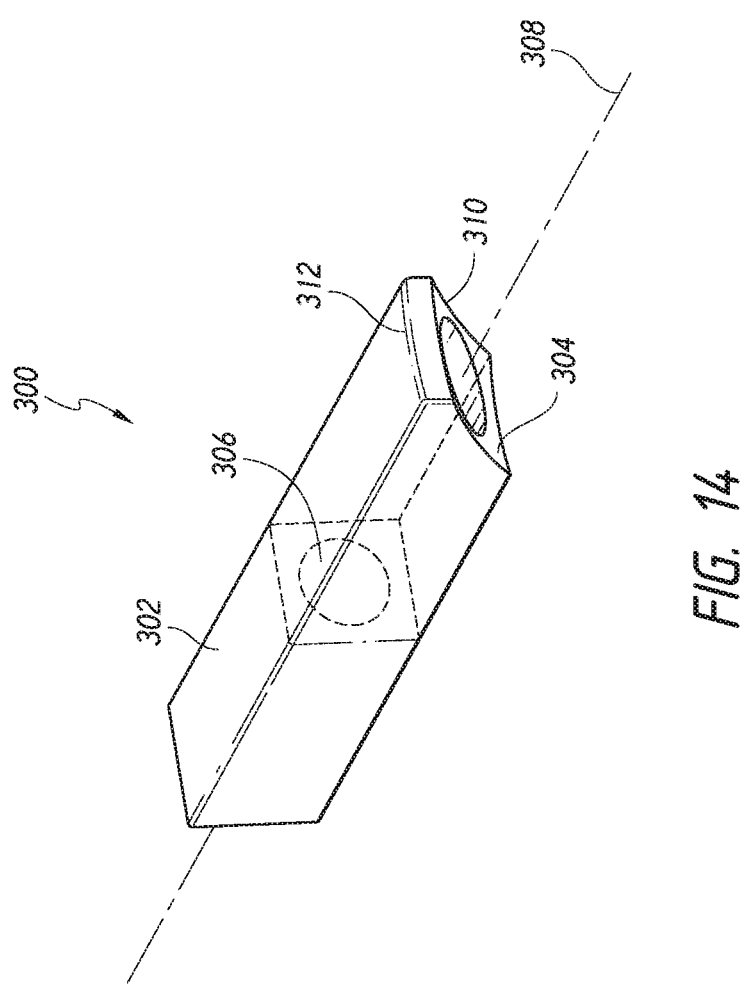
FIG. 14 illustrates a placement device for use with an intraocular implant injector, according to some embodiments.
Figure 16:
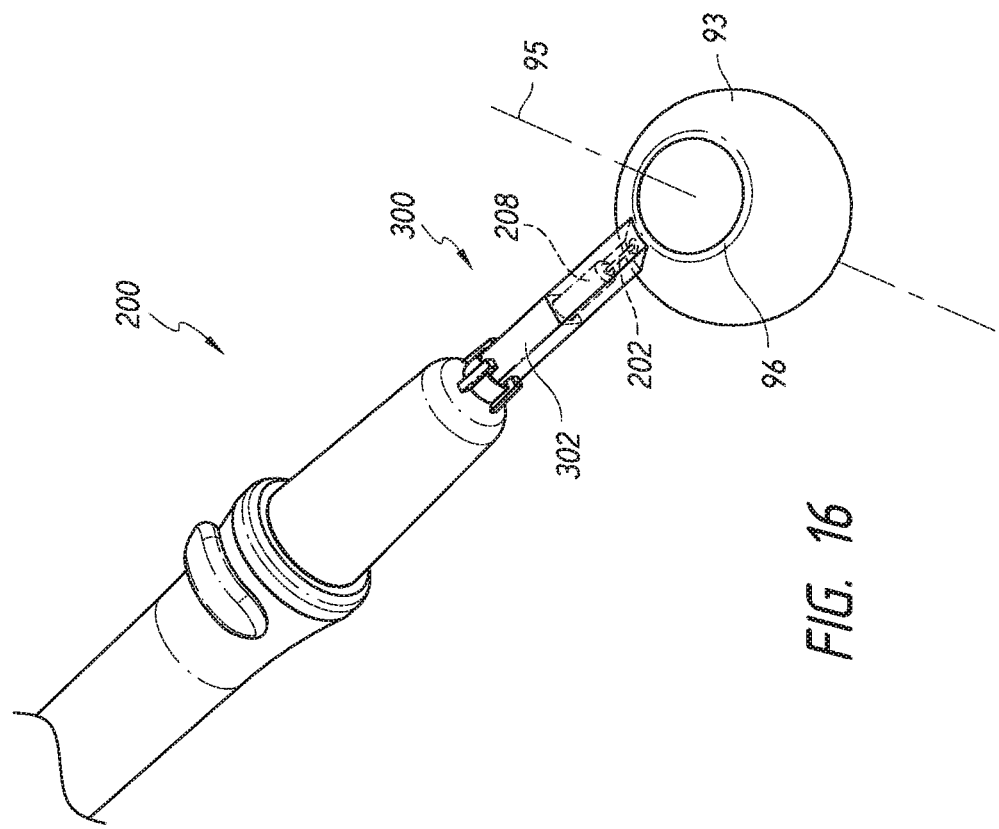
FIGS. 15 and 16 illustrate a procedure for placing an intraocular implant into an eye using an implant injector and the placement device shown in FIG. 14, according to some embodiments.
Figure 15:
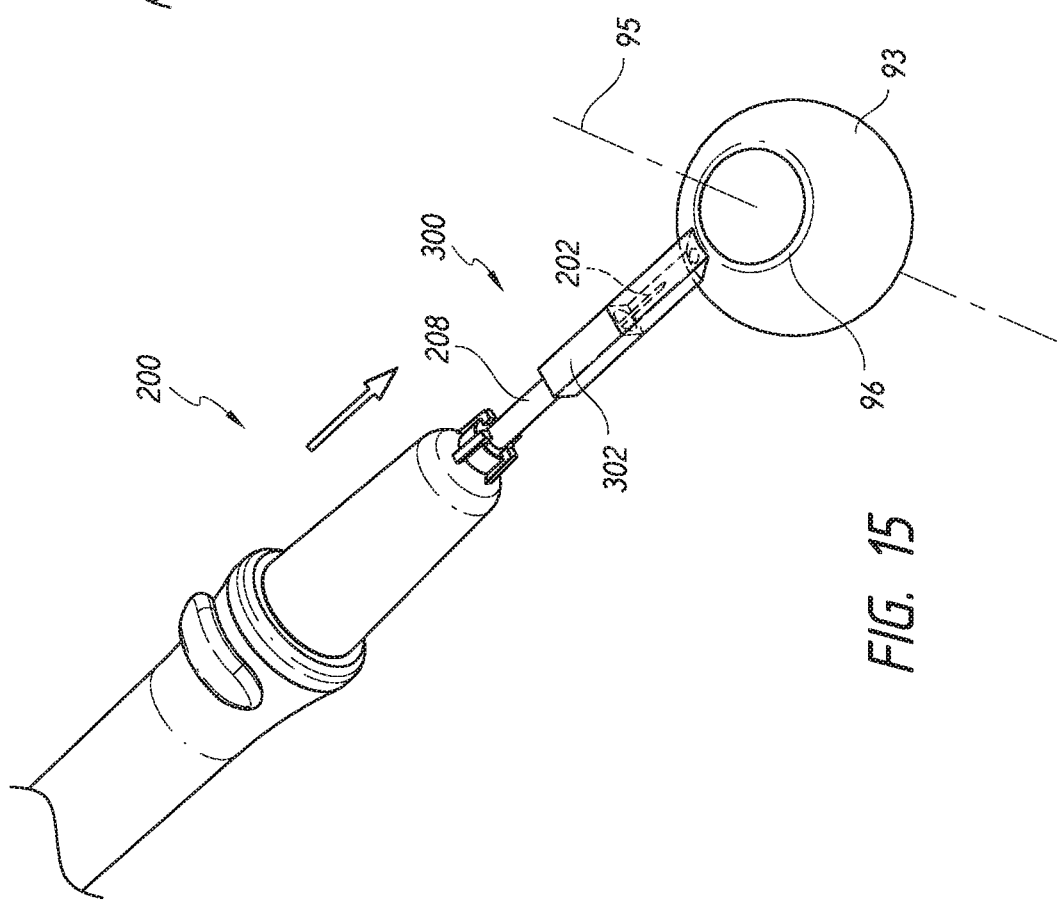

FIGS. 14-16 illustrate embodiments of an intraocular implant injector 200 and a placement device 300. In some embodiments, an intraocular implant injector 200 can be provided in which a placement device 300 and the injector are formed unitarily, coupled with each other, or otherwise formed from a single, continuous housing or material to form a single handheld unit. Otherwise, the placement device 300 can be removably coupled to the injector 200. For example, the placement device 300 can be prepared for use with an injector 200, and in some embodiments, as a retrofit to an existing injector.

FIG. 14 illustrates an embodiment of an intraocular implant placement device 300 comprising a body having proximal and distal portions. A needle support component 302 extends from a proximal portion toward a distal portion of the placement device 300. A distal portion of the placement device 300 can comprise one or more eye-contacting surfaces 304 to facilitate alignment of a needle or injector relative to an eye.

As shown in FIGS. 14-16, the needle support component 302 can accommodate, mate with, or otherwise engage or support a needle 202 and/or a portion of an injector 200. The needle support component 302 can comprise a port 306, such as an elongate aperture, lumen, or bore that defines a needle axis 308 extending from the proximal portion toward the distal portion of the placement device 300. A needle 202, sleeve 208, and/or other portion of an injector 200 can be fitted into the shaft 306 from the proximal portion. In some embodiments, an inner profile of the needle support component 302 can closely match an outer profile of the needle 202, sleeve 208, or other portion of the injector 200.

The eye-contacting surface 304 can be configured for engagement against an external surface of the eye 93 and can comprise at least one surface configured to mate against the eye 93. For example, the surface can comprise a concave or arcuate surface that approximates the external surface of the eye in order to position the placement device 300 against the eye 93. The eye-contacting surface can be configured to facilitate alignment of the placement device 300 with one or more indicia of the eye 93, such as the cornea, the corneal limbus 96, and the pupil.

In some embodiments, the eye-contacting surface 304 can comprise a horizontal radius and a vertical radius. In accordance with some embodiments, when the eye-contacting surface 304 is engaged against the external surface of the eye 93, the vertical radius 310 can be oriented normal relative to the visual axis 95 (pupillary or optical axis) of the eye 93.

In some embodiments, the horizontal upper edge 312 of the placement device 300 that can be aligned with the corneal limbus 96 to facilitate alignment of the placement device 300 relative to the visual axis 95 of the eye 93. In some embodiments, the vertical radius 310 can facilitate alignment of the placement device 300 so that the needle axis 94 intersects the final position of the intraocular implant 100. In some embodiments, the vertical radius 310 can comprise an angle of between about 10 and 60 degrees, between about 20 and 50 degrees, between about 25 and 45 degrees, between about 30 and 40 degrees, or about 35 degrees from horizontal.

Referring to FIG. 15, a needle 202, sleeve 208, or other portion of the injector 200 is permitted to extend through the needle support component 302 from the proximal portion toward the distal portion of the placement device 300. In this pre-injection configuration, the needle 202 does not extend beyond the distal portion of the placement device 300. However, referring to FIG. 16, with the eye-contacting surface 304 engaged against an external surface of the eye 93, the needle 202 can be advanced toward an injection configuration. In moving toward the injection configuration, the needle 202 can be advanced toward the eye 93 such that the needle 202 extends beyond the distal portion of the placement device 300 and into the eye 93. Thereafter, a shunt can be released into the eye using any of the procedures for releasing a shunt from any of the inserters disclosed or referred to herein.

In some embodiments, the placement device 300 can be configured with a longitudinal length so that a distal end of the needle 202 cannot extend a further than predetermined distance beyond the eye-contacting surface 304. The predetermined distance that the needle 202 is permitted to extend beyond the distal portion can be configured to correspond to the maximum distance the implant carried within the needle 202 is to be placed in the eye 93. For example, in the injection configuration, the length of the needle 202 extending beyond the eye-contacting surface 304 can be approximately equal to the distance between the conjunctiva 7 and the anterior chamber 1. In some embodiments, a length of the placement device 300 along the longitudinal needle axis 308 is configured or selected to limit advancement of the needle 202 through the eye-contacting surface 304.

In some embodiments, the placement device 300 can comprise a longitudinal restriction to restrict the needle 202 from travelling further than a predetermined distance beyond the distal portion of the placement device 300. In some embodiments, the longitudinal restriction can comprise a shoulder that contacts a portion of the needle 202, sleeve 208, or other portion of the injector 200 during movement of the needle toward the injection configuration. For example, the placement device 300 can comprise a shoulder positioned within the lumen of the needle support component 302. Thus, the needle 202, sleeve 208, or other portion of the injector 200 moving through the needle support component 302 can be stopped by a shoulder so that the needle 202 advances only to the specified or predetermined distance beyond the distal portion.

In some embodiments, all or at least a portion of the placement device 300 can be transparent. For example, a distal portion of the placement device 300 can be transparent to facilitate visual alignment with an indicium of the eye, monitoring the position of the needle 202, sleeve 208, or other portion of the injector 200, or to otherwise facilitate alignment of the placement device 300 with the eye 93. In some embodiments, the distal portion can comprise a longer cross-sectional width than a proximal portion of the placement device 300. In some embodiments, the distal portion comprises a tapering cross-sectional width.

Pharmaceutical and Biological Agents

As discussed above, the devices and/or methods disclosed herein can provide treatment with a drug or pharmaceutical, such as by implanting an intraocular implant that has been coated, packed, layered, and/or impregnated with a pharmaceutical and/or biological agent, by treating the eye topically with a pharmaceutical and/or biological agent, and/or by injecting a pharmaceutical and/or biological agent into the anterior chamber and/or a target outflow region, including any target outflow regions discussed or referenced herein, prior to or after releasing a implant from the device. In some embodiments, the pharmaceutical and/or biological agent can include an immunosuppressive agent is selected from the group consisting of dexamethasone, cyclosporin A, azathioprine, brequinar, gusperimus, 6-mercaptopurine, mizoribine, rapamycin, tacrolimus (FK-506), folic acid analogs (e.g., denopterin, edatrexate, methotrexate, piritrexim, pteropterin, Tomudex®, trimetrexate), purine analogs (e.g., cladribine, fludarabine, 6-mercaptopurine, thiamiprine, thiaguanine), pyrimidine analogs (e.g., ancitabine, azacitidine, 6-azauridine, carmofur, cytarabine, doxifluridine, emitefur, enocitabine, floxuridine, fluorouracil, gemcitabine, tegafur) fluocinolone, triaminolone, anecortave acetate, fluorometholone, medrysone, and prednislone. In a preferred embodiment, the immunosuppressive agent is dexamethasone. In another preferred embodiment, the immunosuppressive agent is cyclosporin A. In another embodiment, the bioerodible implant comprises more than one immunosuppressive agent.

In some embodiments, the pharmaceutical and/or biological agent can include one or more additional therapeutic agents, such as antibiotics or anti-inflammatory agents, such as antibacterial antibiotics, synthetic antibacterials, antifungal antibiotics, synthetic antifungals, antineoplastics, anti-inflammatory agents, and/or antimicrobial agents.

Antibacterial antibiotics can include aminoglycosides (e.g., amikacin, apramycin, arbekacin, bambermycins, butirosin, dibekacin, dihydrostreptomycin, fortimicin(s), gentamicin, isepamicin, kanamycin, micronomicin, neomycin, neomycin undecylenate, netilmicin, paromomycin, ribostamycin, sisomicin, spectinomycin, streptomycin, tobramycin, trospectomycin), amphenicols (e.g., azidamfenicol, chloramphenicol, florfenicol, thiamphenicol), ansamycins (e.g., rifamide, rifampin, rifamycin sv, rifapentine, rifaximin), β-lactams (e.g., carbacephems (e.g., loracarbef), carbapenems (e.g., biapenem, imipenem, meropenem, panipenem), cephalosporins (e.g., cefaclor, cefadroxil, cefamandole, cefatrizine, cefazedone, cefazolin, cefcapene pivoxil, cefclidin, cefdinir, cefditoren, cefepime, cefetamet, cefixime, cefinenoxime, cefodizime, cefonicid, cefoperazone, cefoxanide, cefotaxime, cefotiam, cefozopran, cefpimizole, cefpiramide, cefpirome, cefpodoxime proxetil, cefprozil, cefroxadine, cefsulodin, ceftazidime, cefteram, ceftezole, ceftibuten, ceftizoxime, ceftriaxone, cefuroxime, cefuzonam, cephacetrile sodium, cephalexin, cephaloglycin, cephaloridine, cephalosporin, cephalothin, cephapirin sodium, cephradine, pivcefalexin), cephamycins (e.g., cefbuperazone, cefinetazole, cefminox, cefotetan, cefoxitin), monobactams (e.g., aztreonam, carumonam, tigemonam), oxacephems, flomoxef, moxalactam), penicillins (e.g., amdinocillin, amdinocillin pivoxil, amoxicillin, ampicillin, apalcillin, aspoxicillin, azidocillin, azlocillin, bacampicillin, benzylpenicillinic acid, benzylpenicillin sodium, carbenicillin, carindacillin, clometocillin, cloxacillin, cyclacillin, dicloxacillin, epicillin, fenbenicillin, floxacillin, hetacillin, lenampicillin, metampicillin, methicillin sodium, mezlocillin, nafcillin sodium, oxacillin, penamecillin, penethamate hydriodide, penicillin g benethamine, penicillin g benzathine, penicillin g benzhydrylamine, penicillin g calcium, penicillin g hydrabamine, penicillin g potassium, penicillin g procaine, penicillin n, penicillin o, penicillin v, penicillin v benzathine, penicillin v hydrabamine, penimepicycline, phenethicillin potassium, piperacillin, pivampicillin, propicillin, quinacillin, sulbenicillin, sultamicillin, talampicillin, temocillin, ticarcillin), other (e.g., ritipenem), lincosamides (e.g., clindamycin, lincomycin), macrolides (e.g., azithromycin, carbomycin, clarithromycin, dirithromycin, erythromycin, erythromycin acistrate, erythromycin estolate, erythromycin glucoheptonate, erythromycin lactobionate, erythromycin propionate, erythromycin stearate, josamycin, leucomycins, midecamycins, miokamycin, oleandomycin, primycin, rokitamycin, rosaramicin, roxithromycin, spiramycin, troleandomycin), polypeptides (e.g., amphomycin, bacitracin, capreomycin, colistin, enduracidin, enviomycin, fusafungine, gramicidin s, gramicidin(s), mikamycin, polymyxin, pristinamycin, ristocetin, teicoplanin, thiostrepton, tuberactinomycin, tyrocidine, tyrothricin, vancomycin, viomycin, virginiamycin, zinc bacitracin), tetracyclines (e.g., apicycline, chlortetracycline, clomocycline, demeclocycline, doxycycline, guamecycline, lymecycline, meclocycline, methacycline, minocycline, oxytetracycline, penimepicycline, pipacycline, rolitetracycline, sancycline, tetracycline), and others (e.g., cycloserine, mupirocin, tuberin).

Synthetic antibacterials can include 2,4-Diaminopyrimidines (e.g., brodimoprim, tetroxoprim, trimethoprim), nitrofurans (e.g., furaltadone, furazolium chloride, nifuradene, nifuratel, nifurfoline, nifurpirinol, nifurprazine, nifurtoinol, nitrofurantoin), quinolones and analogs (e.g., cinoxacin, ciprofloxacin, clinafloxacin, difloxacin, enoxacin, fleroxacin, flumequine, grepafloxacin, lomefloxacin, miloxacin, nadifloxacin, nalidixic acid, norfloxacin, ofloxacin, oxolinic acid, pazufloxacin, pefloxacin, pipemidic acid, piromidic acid, rosoxacin, rufloxacin, sparfloxacin, temafloxacin, tosufloxacin, trovafloxacin), sulfonamides (e.g., acetyl sulfamethoxypyrazine, benzylsulfamide, chloramine-b, chloramine-t, dichloramine t, n2-formylsulfisomidine, n4-β-d-glucosylsulfanilamide, mafenide, 4'-(methylsulfamoyl) sulfanilanilide, noprylsulfamide, phthalylsulfacetamide, phthalylsulfathiazole, salazosulfadimidine, succinylsulfathiazole, sulfabenzamide, sulfacetamide, sulfachlorpyridazine, sulfachrysoidine, sulfacytine, sulfadiazine, sulfadicramide, sulfadimethoxine, sulfadoxine, sulfaethidole, sulfaguanidine, sulfaguanol, sulfalene, sulfaloxic acid, sulfamerazine, sulfameter, sulfamethazine, sulfamethizole, sulfamethomidine, sulfamethoxazole, sulfamethoxypyridazine, sulfametrole, sulfamidochrysoidine, sulfamoxole, sulfanilamide, 4-sulfanilamidosalicylic acid, n4-sulfanilylsulfanilamide, sulfanilylurea, n-sulfanilyl-3,4-xylamide, sulfanitran, sulfaperine, sulfaphenazole, sulfaproxyline, sulfapyrazine, sulfapyridine, sulfasomizole, sulfasymazine, sulfathiazole, sulfathiourea, sulfatolamide, sulfisomidine, sulfisoxazole) sulfones (e.g., acedapsone, acediasulfone, acetosulfone sodium, dapsone, diathymosulfone, glucosulfone sodium, solasulfone, succisulfone, sulfanilic acid, p-sulfanilylbenzylamine, sulfoxone sodium, thiazolsulfone), and others (e.g., clofoctol, hexedine, methenamine, methenamine anhydromethylene-citrate, methenamine hippurate, methenamine mandelate, methenamine sulfosalicylate, nitroxoline, taurolidine, xibomol).

Antifungal antibiotics can include polyenes (e.g., amphotericin b, candicidin, dermostatin, filipin, fungichromin, hachimycin, hamycin, lucensomycin, mepartricin, natamycin, nystatin, pecilocin, perimycin), others (e.g., azaserine, griseofulvin, oligomycins, neomycin undecylenate, pyrrolnitrin, siccanin, tubercidin, viridin).

Synthetic antifungals can include allylamines (e.g., butenafine, naftifine, terbinafine), imidazoles (e.g., bifonazole, butoconazole, chlordantoin, chlormidazole, cloconazole, clotrimazole, econazole, enilconazole, fenticonazole, flutrimazole, isoconazole, ketoconazole, lanoconazole, miconazole, omoconazole, oxiconazole nitrate, sertaconazole, sulconazole, tioconazole), thiocarbamates (e.g., tolciclate, tolindate, tolnaftate), triazoles (e.g., fluconazole, itraconazole, saperconazole, terconazole) others (e.g., acrisorcin, amorolfine, biphenamine, bromosalicylchloranilide, buclosamide, calcium propionate, chlorphenesin, ciclopirox, cloxyquin, coparaffinate, diamthazole dihydrochloride, exalarnide, flucytosine, halethazole, hexetidine, loflucarban, nifuratel, potassium iodide, propionic acid, pyrithione, salicylanilide, sodium propionate, sulbentine, tenonitrozole, triacetin, ujothion, undecylenic acid, zinc propionate).

Antineoplastics can include antibiotics and analogs (e.g., aclacinomycins, actinomycin f1, anthramycin, azaserine, bleomycins, cactinomycin, carubicin, carzinophilin, chromomycins, dactinomycin, daunorubicin, 6-diazo-5-oxo-L-norleucine, doxorubicin, epirubicin, idarubicin, menogaril, mitomycins, mycophenolic acid, nogalamycin, olivomycines, peplomycin, pirarubicin, plicamycin, porfiromycin, puromycin, streptonigrin, streptozocin, tubercidin, zinostatin, zorubicin), antimetabolites (e.g. folic acid analogs (e.g., denopterin, edatrexate, methotrexate, piritrexim, pteropterin, Tomudex®, trimetrexate), purine analogs (e.g., cladribine, fludarabine, 6-mercaptopurine, thiamiprine, thioguanine), pyrimidine analogs (e.g., ancitabine, azacitidine, 6-azauridine, carmofur, cytarabine, doxifluridine, emitefur, enocitabine, floxuridine, fluorouracil, gemcitabine, tagafur).

Anti-inflammatory agents include steroidal and non-steroidal anti-inflammatory agents. Steroidal anti-inflammatory agents can include 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, and triamcinolone hexacetonide.

Non-steroidal anti-inflammatory agents can include aminoarylcarboxylic acid derivatives (e.g., enfenamic acid, etofenamate, flufenamic acid, isonixin, meclofenamic acid, mefenamic acid, niflumic acid, talniflumate, terofenamate, tolfenamic acid), arylacetic acid derivatives (e.g., aceclofenac, acemetacin, alclofenac, amfenac, amtolmetin guacil, bromfenac, bufexamac, cinmetacin, clopirac, diclofenac sodium, etodolac, felbinac, fenclozic acid, fentiazac, glucametacin, ibufenac, indomethacin, isofezolac, isoxepac, lonazolac, metiazinic acid, mofezolac, oxametacine, pirazolac, proglumetacin, sulindac, tiaramide, tolmetin, tropesin, zomepirac), arylbutyric acid derivatives (e.g., bumadizon, butibufen, fenbufen, xenbucin), arylcarboxylic acids (e.g., clidanac, ketorolac, tinoridine), arylpropionic acid derivatives (e.g., alminoprofen, benoxaprofen, bermoprofen, bucloxic acid, carprofen, fenoprofen, flunoxaprofen, flurbiprofen, ibuprofen, ibuproxam, indoprofen, ketoprofen, loxoprofen, naproxen, oxaprozin, piketoprolen, pirprofen, pranoprofen, protizinic acid, suprofen, tiaprofenic acid, ximoprofen, zaltoprofen), pyrazoles (e.g., difenamizole, epirizole), pyrazolones (e.g., apazone, benzpiperylon, feprazone, mofebutazone, morazone, oxyphenbutazone, phenylbutazone, pipebuzone, propyphenazone, ramifenazone, suxibuzone, thiazolinobutazone), salicylic acid derivatives (e.g., acetaminosalol, aspirin, benorylate, bromosaligenin, calcium acetylsalicylate, diflunisal, etersalate, fendosal, gentisic acid, glycol salicylate, imidazole salicylate, lysine acetylsalicylate, mesalamine, morpholine salicylate, 1-naphthyl salicylate, olsalazine, parsalmide, phenyl acetylsalicylate, phenyl salicylate, salacetamide, salicylamide o-acetic acid, salicyl sulfuric acid, salsalate, sulfasalazine), thiazinecarboxamides (e.g., ampiroxicam, droxicam, isoxicam, lomoxicam, piroxicam, tenoxicam), ε-acetamidocaproic acid, s-adenosylmethionine, 3-amino-4-hydroxybutyric acid, amixetrine, bendazac, benzydamine, a-bisabolol, bucolome, difenpiramide, ditazol, emorfazone, fepradinol, guaiazulene, nabumetone, nimesulide, oxaceprol, paranyline, perisoxal, proquazone, superoxide dismutase, tenidap, and zileuton.

Antimicrobial agents can include antibiotics, antiseptics, disinfectants, and/or other synthetic moieties, and combinations thereof, that are soluble in organic solvents such as alcohols, ketones, ethers, aldehydes, acetonitrile, acetic acid, formic acid, methylene chloride and chloroform.

Illustration of Subject Technology as Clauses

Various examples of aspects of the disclosure are described as numbered clauses (1, 2, 3, etc.) for convenience. These are provided as examples, and do not limit the subject technology. Identifications of the figures and reference numbers are provided below merely as examples and for illustrative purposes, and the clauses are not limited by those identifications.

Clause 1. An intraocular implant for delivery of a drug to an eye, the implant comprising: an elongate body configured to be advanced into the eye through conjunctiva and sclera of the eye, the elongate body comprising a longitudinal length such that upon placement within the eye, a first portion of the implant is within an anterior chamber of the eye, and a second portion of the implant is within an intrascleral space of the eye; and a drug deliverable from the implant to the eye.

Clause 2. The implant of the preceding Clause, wherein the elongate body comprises a resilient material impregnated with the drug, the drug configured to be released from the implant to the eye.

Clause 3. The implant of any of the preceding Clauses, wherein the elongate body comprises a rigid material coated on an outer surface with a resilient material, the resilient material configured to engage against the eye to reduce and/or avoid migration of implant.

Clause 4. The implant of any of the preceding Clauses, wherein the resilient material is impregnated with the drug, the drug configured to be released from the implant to the eye.

Clause 5. The implant of any of the preceding Clauses, wherein the elongate body comprises a first passage in communication with a cavity within the elongate body, the cavity comprising the drug, wherein the drug is configured to be released from the cavity through the first passage.

Clause 6. The implant of any of the preceding Clauses, wherein the first passage comprises a membrane configured to permit release of the drug from the implant at a predetermined rate.

Clause 7. The implant of any of the preceding Clauses, wherein the first passage comprises a slit through the elongate body between the first and second portions of the implant.

Clause 8. The implant of any of the preceding Clauses, wherein the first passage extends through the first portion, and a second passage, in communication with the cavity, extends through the second portion, wherein the drug is configured to be released from the cavity through at least one of the first and second passages.

Clause 9. The implant of any of the preceding Clauses, wherein the first and second passages comprise a membrane configured to permit release of the drug from the implant at a predetermined rate.

Clause 10. The implant of any of the preceding Clauses, wherein an outer surface of the elongate body is tapered to reduce and/or avoid migration of the elongate body deep to the sclera, the elongate body having a cross-sectional width at the first portion that is less than a cross-sectional width at the second portion.

Clause 11. The implant of any of the preceding Clauses, wherein an outer surface of the elongate body comprises a protrusion to reduce and/or avoid migration of the elongate body deep to the sclera.

Clause 12. The implant of Clause 11, wherein the protrusion is proximate to the second portion of the elongate body.

Clause 13. The implant of Clause 11, wherein the protrusion comprises a barb.

Clause 14. The implant of Clause 11, wherein the protrusion comprises a ridge.

Clause 15. The implant of any of the preceding Clauses, wherein the elongate body comprises a longitudinal length defining a lumen extending through the first and second portions, the drug is retained within the lumen and configured to be released from the implant to the eye.

Clause 16. The implant of any of the preceding Clauses, wherein the lumen is obstructed by the drug to permit fluid flow through the lumen after the drug is sufficiently released from the implant to define a passage between the first and second portions.

Clause 17. The implant of any of the preceding Clauses, wherein the lumen is coated with the drug to permit drug elution via fluid flow through the lumen.

Clause 18. An intraocular implant for delivery of a drug to an eye, the implant comprising: an elongate body configured to be advanced within a needle through a conjunctiva, a Tenon capsule, and a sclera of the eye, the elongate body comprising a tapered outer surface to reduce and/or avoid migration of the elongate body deep to the sclera, the elongate body having a cross-sectional width at a first portion that is less than a cross-sectional width at a second portion; and a drug deliverable from the implant to the eye.

Clause 19. The implant of the preceding Clause, wherein the elongate body comprises a resilient material impregnated with the drug, the drug configured to be released from the implant to the eye.

Clause 20. The implant of any of the preceding Clauses, wherein the elongate body comprises a rigid material coated on an outer surface with a resilient material, the resilient material configured to engage against the eye to reduce and/or avoid migration of implant.

Clause 21. The implant of any of the preceding Clauses, wherein the resilient material is impregnated with the drug, the drug configured to be released from the implant to the eye.

Clause 22. The implant of any of the preceding Clauses, wherein the first portion comprises a first passage in communication with a cavity within the elongate body, the cavity comprising the drug, wherein the drug is configured to be released from the cavity through the first passage.

Clause 23. The implant of any of the preceding Clauses, wherein the first passage comprises a membrane configured to permit release of the drug from the implant at a predetermined rate.

Clause 24. The implant of any of the preceding Clauses, wherein the first passage extends through the first portion, and a second passage, in communication with the cavity, extends through the second portion, wherein the drug is configured to be released from the cavity through at least one of the first and second passages.

Clause 25. An ab externo method of placing an intraocular implant into an eye, the method comprising the steps of: advancing a needle, in which the implant is disposed, into the eye through conjunctiva and sclera of the eye, the implant comprising a drug deliverable to the eye; and releasing the intraocular implant to anchor the implant within an intrascleral space of the eye.

Clause 26. The method of the preceding Clause, wherein when released, a proximal end of the implant is positioned within the sclera.

Clause 27. The method of any of the preceding Clauses, wherein the releasing comprises positioning a first portion of the implant within an anterior chamber of the eye and a second portion of the implant within the intrascleral space.

Clause 28. The method of any of the preceding Clauses, wherein the advancing comprises advancing the needle through Tenon's capsule.

Clause 29. The method of any of the preceding Clauses, wherein advancing the needle further comprises advancing a pusher rod within the needle to position the implant at a distal portion of the needle.

Clause 30. The method of any of the preceding Clauses, comprising positioning a bevel of the needle within an anterior chamber of the eye while advancing the pusher rod to advance a first portion of the implant through the bevel of the needle while permitting a second portion of the implant to remain within the needle.

Clause 31. The method of any of the preceding Clauses, further comprising withdrawing the needle relative to the pusher rod while maintaining the pusher rod stationary relative to the eye to retain the first portion of the implant within the anterior chamber of the eye.

Clause 32. The method of any of the preceding Clauses, positioning a bevel of the needle within an anterior chamber of the eye.

Clause 33. The method of any of the preceding Clauses, wherein the positioning comprises orienting a longitudinal axis of the needle at an angle relative to a visual axis of the eye to facilitate placement of a second portion of the implant deep to a superficial layer of the sclera and a first portion of the implant within the anterior chamber of the eye.

Clause 34. The method of Clause 33, wherein the angle is between about 10 degrees and about 60 degrees.

Clause 35. The method of Clause 33, wherein the angle is between about 20 degrees and about 50 degrees.

Clause 36. The method of Clause 33, wherein the angle is between about 25 degrees and about 40 degrees.

Clause 37. The method of Clause 33, wherein the angle is between about 30 degrees and about 35 degrees.

Clause 38. The method of Clause 33, wherein the angle is about 30 degrees.

Clause 39. The method of any of the preceding Clauses, wherein upon release, a first end of the implant is positioned within an anterior chamber of the eye and a second end of the implant is positioned at least about 0.25-0.5 mm deep to a superficial wall of the sclera.

Clause 40. The method of any of the preceding Clauses, wherein upon release, a proximal end of the implant is positioned at least about 0.25-0.5 mm deep to a superficial wall of the sclera.

Clause 41. The method of any of the preceding Clauses, wherein upon release, a first end of the implant is positioned within the anterior chamber and a second end of the implant is positioned at least about 0.5-0.75 mm deep to a superficial wall of the sclera.

Clause 42. The method of any of the preceding Clauses, wherein upon release, a proximal end of the implant is positioned at least about 0.5-0.75 mm deep to a superficial wall of the sclera.

Clause 43. The method of any of the preceding Clauses, further comprising the step of contacting a sleeve, coupled to the needle, against an external surface of the eye, to restrict further longitudinal advancement of the needle into the eye.

Clause 44. The method of any of the preceding Clauses, wherein the releasing comprises releasing the intraocular implant to anchor a first portion of the implant deep to the sclera and a second portion of the implant within an intrascleral space of the eye.

Clause 45. The method of any of the preceding Clauses, wherein the positioning comprises positioning the second portion of the implant between layers of the sclera.

Clause 46. The method of any of the preceding Clauses, comprising positioning a bevel of the needle within an anterior chamber of the eye and an outflow portion of the implant within the anterior chamber.

Clause 47. The method of any of the preceding Clauses, comprising positioning a bevel of the needle within a choroidal space of the eye and an outflow portion of the implant within the choroidal space.

Clause 48. The method of any of the preceding Clauses, comprising positioning a bevel of the needle within a vitreous space of the eye and an outflow portion of the implant within the vitreous space.

Clause 49. The method of any of the preceding Clauses, wherein the implant comprises a tapered cross-sectional profile, the releasing comprising anchoring the implant by positioning a larger cross-sectional profile first end portion of the implant superficially within the sclera and a smaller cross-sectional profile second end portion deep to the first end portion.

Clause 50. The method of any of the preceding Clauses, wherein the implant comprises a conical shape in which the first end portion of the implant has a larger cross-sectional profile than the second end portion.

Clause 51. The method of any of the preceding Clauses, wherein the implant comprises at least one engagement protrusion disposed along a proximal, outer region of the implant, the releasing comprising anchoring the implant by positioning the engagement protrusion between layers of sclera.

Clause 52. The method of any of the preceding Clauses, wherein the at least one engagement protrusion comprises a hook, ridge, barb, spike, wing, or bump.

Clause 53. The method of any of the preceding Clauses, wherein the implant comprises an intraocular shunt.

Clause 54. The method of any of the preceding Clauses, further comprising positioning a proximal end of the implant within a target outflow region and a distal end of the implant within an anterior chamber of the eye.

Clause 55. The method of any of the preceding Clauses, wherein the implant comprises an intraocular shunt and the drug coats the shunt or fills a lumen of the shunt.

Clause 56. The method of any of the preceding Clauses, wherein the implant comprises a soft biocompatible material.

Clause 57. The method of any of the preceding Clauses, wherein the implant comprises a soft polymer material.

Clause 58. The method of any of the preceding Clauses, wherein the implant comprises a gelatin material.

Clause 59. An intraocular implant placement device for placing an intraocular implant into an eye, the device comprising: a body comprising proximal and distal portions and a longitudinal needle axis extending between the proximal and distal portions, the proximal portion configured to couple with an intraocular implant injector to permit a needle of the implant injector to extend along the longitudinal needle axis, and the distal portion comprising an eye-contacting surface configured to engage the eye to permit a clinician to align the placement device relative to an indicium of the eye thereby aligning the needle relative to the eye.

Clause 60. The placement device of the preceding Clause, wherein a length of the body along the longitudinal needle axis is selected to limit advancement of the needle through the eye-contacting surface.

Clause 61. The placement device of any of the preceding Clauses, wherein the body obstructs advancement of the needle distal to the eye-contacting surface beyond a predetermined length.

Clause 62. The placement device of any of the preceding Clauses, wherein the eye-contacting surface comprises at least one arcuate surface for alignment of the placement device relative to an indicium of the eye and alignment of the longitudinal needle axis to the eye.

Clause 63. The placement device of any of the preceding Clauses, wherein the eye-contacting surface is at least partially concave.

Clause 64. The placement device of any of the preceding Clauses, wherein the distal portion flares outwardly.

Clause 65. The placement device of any of the preceding Clauses, wherein the eye-contacting surface extends from an arcuate edge of the distal portion, the arcuate edge being positionable adjacent to a corneal limbus of the eye for aligning the placement device relative to the eye.

Clause 66. The placement device of any of the preceding Clauses, wherein the eye-contacting surface extends proximally from a distal end of the body.

Clause 67. The placement device of any of the preceding Clauses, wherein when coupled with the implant injector, the needle of the implant injector is coaxial with the longitudinal needle axis.

Clause 68. The placement device of any of the preceding Clauses, wherein the placement device is detachable from an implant injector.

Clause 69. The placement device of any of the preceding Clauses, wherein the body surrounds at least a portion of the needle.

Clause 70. The placement device of any of the preceding Clauses, wherein the body comprises an elongate shaft and a needle port extending therethrough.

Clause 71. The placement device of any of the preceding Clauses, wherein the needle port extends through the eye-contacting surface.

Clause 72. The placement device of any of the preceding Clauses, wherein the longitudinal needle axis extends through the eye-contacting surface.

Clause 73. The placement device of any of the preceding Clauses, wherein the eye-contacting surface comprises a blunt face positionable against the eye, the blunt face having a surface area of at least about 5 mm$^2$.

Clause 74. The placement device of any of the preceding Clauses, wherein eye-contacting surface comprises a blunt face positionable against the eye, the blunt face having a surface area of at least about 10 mm$^2$.

Clause 75. The placement device of any of the preceding Clauses, wherein eye-contacting surface comprises a single, continuous surface through which the needle axis passes.

Clause 76. The placement device of any of the preceding Clauses, wherein a portion of the body is transparent to facilitate visualization of the needle or an indicium of the eye.

Further Considerations

In some embodiments, any of the clauses herein may depend from any one of the independent clauses or any one of the dependent clauses. In one aspect, any of the clauses (e.g., dependent or independent clauses) may be combined with any other one or more clauses (e.g., dependent or independent clauses). In one aspect, a claim may include some or all of the words (e.g., steps, operations, means or components) recited in a clause, a sentence, a phrase or a paragraph. In one aspect, a claim may include some or all of the words recited in one or more clauses, sentences, phrases or paragraphs. In one aspect, some of the words in each of the clauses, sentences, phrases or paragraphs may be removed. In one aspect, additional words or elements may be added to a clause, a sentence, a phrase or a paragraph. In one aspect, the subject technology may be implemented without utilizing some of the components, elements, functions or operations described herein. In one aspect, the subject technology may be implemented utilizing additional components, elements, functions or operations.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

In one or more aspects, the terms "about," "substantially," and "approximately" may provide an industry-accepted tolerance for their corresponding terms and/or relativity between items, such as from less than one percent to 10 percent.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

Although the detailed description contains many specifics, these should not be construed as limiting the scope of the subject technology but merely as illustrating different examples and aspects of the subject technology. It should be appreciated that the scope of the subject technology includes other embodiments not discussed in detail above. Various other modifications, changes and variations may be made in the arrangement, operation and details of the method and apparatus of the subject technology disclosed herein without departing from the scope of the present disclosure. Unless otherwise expressed, reference to an element in the singular is not intended to mean "one and only one" unless explicitly stated, but rather is meant to mean "one or more." In addition, it is not necessary for a device or method to address every problem that is solvable (or possess every advantage that is achievable) by different embodiments of the disclosure in order to be encompassed within the scope of the disclosure. The use herein of "can" and derivatives thereof shall be understood in the sense of "possibly" or "optionally" as opposed to an affirmative capability.

What is claimed is:

1. An ab externo method of placing an intraocular implant into an eye, the method comprising the steps of:
    advancing a needle, in which the implant is disposed, into the eye through conjunctiva, Tenon's capsule, and sclera of the eye, the implant comprising a drug deliverable to the eye; and
    releasing the intraocular implant to anchor the implant within an intrascleral space of the eye, wherein the implant functions as a plug to obstruct fluid flow from an anterior chamber of the eye toward the intrascleral space upon release.

2. The method of claim 1, wherein when released, a proximal end of the implant is positioned within the sclera.

3. The method of claim 1, wherein the releasing comprises positioning a first portion of the implant within an anterior chamber of the eye and a second portion of the implant within the intrascleral space.

4. The method of claim 1, wherein advancing the needle further comprises advancing a pusher rod within the needle to position the implant at a distal portion of the needle.

5. The method of claim 4, comprising positioning a bevel of the needle within an anterior chamber of the eye while advancing the pusher rod to advance a first portion of the implant through the bevel of the needle while permitting a second portion of the implant to remain within the needle.

6. The method of claim 1, comprising positioning a bevel of the needle within an anterior chamber of the eye.

7. The method of claim 6, wherein the positioning comprises orienting a longitudinal axis of the needle at an angle relative to a visual axis of the eye to facilitate placement of a second portion of the implant deep to a superficial layer of the sclera and a first portion of the implant within the anterior chamber of the eye.

8. The method of claim 1, further comprising the step of contacting a sleeve, coupled to the needle, against an external surface of the eye, to restrict further longitudinal advancement of the needle into the eye.

9. The method of claim 1, comprising positioning a bevel of the needle within a choroidal space of the eye and a first portion of the implant within the choroidal space.

10. The method of claim 1, comprising positioning a bevel of the needle within a vitreous space of the eye and a first portion of the implant within the vitreous space.

11. The method of claim 1, wherein the implant comprises a tapered cross-sectional profile, the releasing comprising anchoring the implant by positioning a larger cross-sectional profile first end portion of the implant superficially within the sclera and a smaller cross-sectional profile second end portion deep to the first end portion.

12. The method of claim 1, wherein the implant is configured to elute the drug therefrom to permit flow from the anterior chamber after obstructing flow therefrom.

13. An ab externo method of placing an intraocular implant into an eye, the method comprising the steps of:
    advancing a needle, in which the implant is disposed, into the eye through conjunctiva and sclera of the eye, the implant comprising a drug deliverable to the eye, the implant comprising a tapered cross-sectional profile; and
    releasing the intraocular implant to anchor the implant within an intrascleral space of the eye by positioning a larger cross-sectional profile first end portion of the implant superficially within the sclera and a smaller cross-sectional profile second end portion deep to the first end portion.

14. The method of claim 13, wherein advancing the needle further comprises advancing a pusher rod within the needle to position the implant at a distal portion of the needle.

15. The method of claim 14, comprising positioning a bevel of the needle within an anterior chamber of the eye while advancing the pusher rod to advance the first end portion of the implant through the bevel of the needle while permitting the second end portion of the implant to remain within the needle.

16. The method of claim 13, positioning a bevel of the needle within an anterior chamber of the eye.

17. The method of claim 16, wherein the releasing comprises positioning the second end portion of the implant within the anterior chamber of the eye.

18. The method of claim 13, further comprising the step of contacting a sleeve, coupled to the needle, against an external surface of the eye, to restrict further longitudinal advancement of the needle into the eye.

19. An ab externo method of placing an intraocular implant into an eye, the method comprising the steps of:
    advancing a needle, in which the implant is disposed, into the eye through conjunctiva and sclera of the eye, the implant comprising a drug deliverable to the eye;
    positioning a bevel of the needle (i) within a choroidal space of the eye and an outflow portion of the implant within the choroidal space or (ii) within a vitreous space of the eye and the outflow portion of the implant within the vitreous space; and
    releasing the intraocular implant to anchor the implant within an intrascleral space of the eye, wherein the implant functions as a plug to obstruct fluid flow from an anterior chamber of the eye toward the intrascleral space upon release.

20. The method of claim 19, wherein the implant comprises a tapered cross-sectional profile, the releasing comprising anchoring the implant by positioning a larger cross-sectional profile first end portion of the implant superficially within the sclera and a smaller cross-sectional profile second end portion deep to the first end portion.

21. The method of claim 19, wherein the implant comprises a conical shape in which a first end portion of the implant has a larger cross-sectional profile than a second end portion.

22. The method of claim 12, wherein the elution of the drug opens a lumen through the implant.

* * * * *